(12) United States Patent
Godavarti et al.

(10) Patent No.: US 7,820,799 B2
(45) Date of Patent: *Oct. 26, 2010

(54) METHODS OF PURIFYING FC REGION CONTAINING PROTEINS

(75) Inventors: Ranganathan Godavarti, Burlington, MA (US); Timothy Iskra, Derry, NH (US)

(73) Assignees: Janssen Alzheimer Immunotherapy, Little Island, County Cork (IE); Wyeth LLC, Madison, NJ (US)

( * ) Notice: Subject to any disclaimer, the term of this patent is extended or adjusted under 35 U.S.C. 154(b) by 131 days.

This patent is subject to a terminal disclaimer.

(21) Appl. No.: 11/455,203

(22) Filed: Jun. 16, 2006

(65) Prior Publication Data

US 2007/0072307 A1 Mar. 29, 2007

Related U.S. Application Data

(60) Provisional application No. 60/691,821, filed on Jun. 17, 2005.

(51) Int. Cl.
*C07K 1/22* (2006.01)
(52) U.S. Cl. .................. 530/390.5; 424/177.1; 530/413
(58) Field of Classification Search ........................ None
See application file for complete search history.

(56) References Cited

U.S. PATENT DOCUMENTS

| | | | |
|---|---|---|---|
| 4,676,980 A | 6/1987 | Segal et al. | |
| 4,816,567 A | 3/1989 | Cabilly et al. | |
| 4,851,341 A | 7/1989 | Hopp et al. | |
| 5,112,952 A * | 5/1992 | Mallia et al. ............. | 530/387.1 |
| 5,116,964 A | 5/1992 | Capon et al. | |
| 5,223,409 A | 6/1993 | Ladner et al. | |
| 5,225,538 A | 7/1993 | Capon et al. | |
| 5,225,539 A | 7/1993 | Winter | |
| 5,336,603 A | 8/1994 | Capon et al. | |
| 5,428,130 A | 6/1995 | Capon et al. | |
| 5,770,429 A | 6/1998 | Lonberg et al. | |
| 5,786,180 A | 7/1998 | Konig et al. | |
| 6,114,598 A | 9/2000 | Kucherlapati et al. | |
| 6,150,584 A | 11/2000 | Kucherlapati et al. | |
| 6,420,113 B1 | 7/2002 | Buechler et al. | |
| 6,710,226 B1 | 3/2004 | Schenk | |
| 6,743,427 B1 | 6/2004 | Schenk | |
| 6,750,324 B1 | 6/2004 | Schenk et al. | |
| 6,761,888 B1 | 7/2004 | Schenk | |
| 6,787,138 B1 | 9/2004 | Schenk | |
| 6,787,139 B1 | 9/2004 | Schenk | |
| 6,787,140 B1 | 9/2004 | Schenk | |
| 6,787,143 B1 | 9/2004 | Schenk | |
| 6,787,144 B1 | 9/2004 | Schenk | |
| 6,787,523 B1 | 9/2004 | Schenk | |
| 6,787,637 B1 | 9/2004 | Schenk et al. | |
| 6,808,712 B2 | 10/2004 | Schenk | |
| 6,818,218 B2 | 11/2004 | Schenk | |
| 6,866,849 B2 | 3/2005 | Schenk | |
| 6,866,850 B2 | 3/2005 | Schenk | |
| 6,870,034 B2 * | 3/2005 | Breece et al. ............... | 530/413 |
| 6,875,434 B1 | 4/2005 | Schenk | |
| 6,890,535 B1 | 5/2005 | Schenk | |
| 6,905,686 B1 | 6/2005 | Schenk | |
| 6,913,745 B1 | 7/2005 | Schenk | |
| 6,936,246 B1 | 8/2005 | Schenk | |
| 6,946,135 B2 | 9/2005 | Schenk | |
| 6,962,707 B2 | 11/2005 | Schenk | |
| 6,972,127 B2 | 12/2005 | Schenk | |
| 6,982,084 B2 | 1/2006 | Schenk | |
| 7,014,855 B2 | 3/2006 | Schenk | |
| 7,179,892 B2 | 2/2007 | Basi | |
| 7,189,819 B2 | 3/2007 | Basi | |
| 7,256,273 B2 | 8/2007 | Basi | |
| 7,575,880 B1 | 8/2009 | Schenk et al. | |
| 7,582,733 B2 | 9/2009 | Basi et al. | |
| 7,588,766 B1 | 9/2009 | Schenk | |
| 7,625,560 B2 | 12/2009 | Basi | |
| 7,635,473 B2 | 12/2009 | Warne et al. | |
| 2003/0165496 A1 | 9/2003 | Basi et al. | |
| 2004/0043418 A1 | 3/2004 | Holtzman et al. | |

(Continued)

FOREIGN PATENT DOCUMENTS

EP 0125023 B1 11/1984

(Continued)

OTHER PUBLICATIONS

Amersham Biosciences, "Antibody Purification, Handbook," retrieved online at www.chromatography.amershambiosciences.com (2002).

(Continued)

*Primary Examiner*—David A Saunders
(74) *Attorney, Agent, or Firm*—Alston & Bird LLP

(57) ABSTRACT

The present application provides methods of purifying polypeptides having a Fc region, for example, antibodies or antibody fusions, by adsorbing the polypeptides to a Fc binding agent, such as, for example, Protein A or Protein G, followed by a wash with a divalent cation salt buffer to remove impurities and subsequent recovery of the adsorbed polypeptides. The present application also features methods of eluting the purified polypeptide as well as the incorporation of the methods within a purification train. Kits comprising components for carrying out the methods and instructions for use are also provided.

86 Claims, No Drawings

U.S. PATENT DOCUMENTS

| | | | |
|---|---|---|---|
| 2004/0081657 | A1 | 4/2004 | Schenk |
| 2004/0082762 | A1 | 4/2004 | Basi et al. |
| 2004/0087777 | A1 | 5/2004 | Basi et al. |
| 2004/0192898 | A1 | 9/2004 | Jia et al. |
| 2004/0229330 | A1 | 11/2004 | Bettencourt et al. |
| 2005/0013815 | A1 | 1/2005 | Schenk |
| 2005/0019330 | A1 | 1/2005 | Schenk |
| 2005/0059802 | A1 | 3/2005 | Schenk et al. |
| 2005/0090648 | A1 | 4/2005 | Tsurushita et al. |
| 2005/0107594 | A1* | 5/2005 | Sun et al. .............. 530/387.1 |
| 2005/0118651 | A1 | 6/2005 | Basi et al. |
| 2005/0142131 | A1 | 6/2005 | Hinton et al. |
| 2005/0169925 | A1 | 8/2005 | Bardroff et al. |
| 2005/0249723 | A1* | 11/2005 | Lazar .............. 424/133.1 |
| 2006/0029611 | A1 | 2/2006 | Schenk |
| 2006/0034858 | A1 | 2/2006 | Schenk |
| 2006/0099206 | A1 | 5/2006 | Sinacore et al. |
| 2006/0194953 | A1 | 8/2006 | Bonnerjea et al. |
| 2006/0198851 | A1 | 9/2006 | Basi |
| 2006/0210557 | A1 | 9/2006 | Luisi et al. |
| 2007/0072307 | A1 | 3/2007 | Godavarti et al. |
| 2007/0082367 | A1 | 4/2007 | Godavarti et al. |
| 2007/0134762 | A1 | 6/2007 | Arumugham et al. |
| 2007/0154480 | A1 | 7/2007 | Schenk et al. |
| 2007/0161088 | A1 | 7/2007 | Arumugham et al. |
| 2008/0096818 | A1 | 4/2008 | Schenk et al. |
| 2008/0145373 | A1 | 6/2008 | Arumugham |
| 2008/0221306 | A1 | 9/2008 | Basi |
| 2008/0227718 | A1 | 9/2008 | Schenk |
| 2008/0279873 | A1 | 11/2008 | Seubert |
| 2008/0292625 | A1 | 11/2008 | Schroeter |
| 2008/0299074 | A1 | 12/2008 | Arumugham |
| 2009/0069544 | A1 | 3/2009 | Basi |
| 2009/0142270 | A1 | 6/2009 | Schroeter et al. |
| 2009/0155256 | A1 | 6/2009 | Black et al. |
| 2009/0191231 | A1 | 7/2009 | Schenk |
| 2009/0285806 | A1 | 11/2009 | Sinacore et al. |
| 2009/0297511 | A1 | 12/2009 | Schenk |

FOREIGN PATENT DOCUMENTS

| | | |
|---|---|---|
| EP | 0323027 A2 | 7/1989 |
| EP | 1601697 B1 | 12/2005 |
| WO | WO-87/02671 A1 | 5/1987 |
| WO | WO-93/08829 A1 | 5/1993 |
| WO | WO-01/62801 A2 | 8/2001 |
| WO | WO-02/46237 A2 | 6/2002 |
| WO | WO-02/088306 A2 | 11/2002 |
| WO | WO-02/088307 A2 | 11/2002 |
| WO | WO-03/015691 A2 | 2/2003 |
| WO | WO-03/016466 A2 | 2/2003 |
| WO | WO-03/070760 A2 | 8/2003 |
| WO | WO-03/077858 A2 | 9/2003 |
| WO | WO-2004/080419 A2 | 9/2004 |
| WO | WO-2004/108895 A2 | 12/2004 |
| WO | WO-2006/066049 A2 | 6/2006 |
| WO | WO-2006/066089 A1 | 6/2006 |
| WO | WO-2006/066171 A1 | 6/2006 |
| WO | WO-2006/138553 A2 | 12/2006 |

OTHER PUBLICATIONS

International Search Report for Application No. PCT/US2006/023478, dated Dec. 29, 2006.

International Preliminary Report on Patentability and Written Opinion for Application No. PCT/US2006/023478, dated Dec. 17, 2007.

Eliasson, Margareta et al, "Chimeric IgG-binding Receptors Engineered from Staphylococcal Protein A and Streptococcal Protein G," *The Journal of Biological Chemistry*, vol. 263(9):4323-4327 (1988).

Hay, Beverly N. et al, "Bacteriophage cloning and *Escherichia coli* expression of a human IgM Fab," *Hum. Antibod. Hybridomas*, vol. 3:81-85 (1992).

Hoogenboom, Hennie R. et al, "Multi-subunit proteins on the surface of filamentous phage: methodologies for displaying antibody (Fab) heavy and light chains," *Nucleic Acids Research*, vol. 19(15):4133-4137 (1991).

Liu, Alvin Y. et al, "Chimeric mouse-human IgG1 antibody that can mediate lysis of cancer cells," *Proc. Natl. Acad. Sci. USA*, vol. 84:3439-3443 (1987).

Milstein, C. et al, "Hybrid hybridomas and their use in immunohistochemistry," *Nature*, vol. 305:537-540 (1983).

Oi, Vernon T. et al, "Chimeric Antibodies," *BioTechniques*, vol. 4(3):214-221 (1986).

Sikkema, W. Dirk, "An Fc-binding protein," *Amer. Biotech. Lab.*, vol. 7:42 (1989).

Traunecker, André et al, "Bispecific single chain molecules (Janusins) target cytotoxic lymphocytes on HIV infected cells," *The EMBO Journal*, vol. 10(12):3655-3659 (1991).

"Chaotropism," Stedman's Medical Dictionary, 27th Edition, Lippincott Williams and Wilkins (2000).

Amersham Biosciences, "Q Sepharose™ High Performance and SP Sepharose High Performance," retrieved online at http://www4.gelifesciences.com/aptrix/upp00919.nsf/Content/WD:Q+Sepharose+Hig(1521788 76-R350) (2002).

Bales, K.R. et al, "Administration of an Anti-Aβ Fab Fragment to APPV717F Transgenic Mice Reduces Neuritic Plaque," *Therapeutics and Therapeutic Strategies*, Poster Session P4-396, p. S587.

Bard, Frédérique et al, "Epitope and isotype specificities of antibodies to β-amyloid peptide for protection against Alzheimer's disease-like neuropathology," *PNAS*, vol. 100(4):2023-2028 (2003).

Bard, Frédérique et al, "Peripherally administered antibodies against amyloid β-peptide enter the central nervous system and reduce pathology in a mouse model of Alzheimer disease," *Nature Medicine*, vol. 6(8):916-919 (2000).

Bussière, Thierry et al, "Morphological Characterization of Thioflavin-S-Positive Amyloid Plaques in Transgenic Alzheimer Mice and Effect of Passive Aβ Immunotherapy on Their Clearance," *American Journal of Pathology*, vol. 165(3):987-995 (2004).

Buttini, Manuel et al, "β-Amyloid Immunotherapy Prevents Synaptic Degeneration in a Mouse Model of Alzheimer's Disease," *The Journal of Neuroscience*, vol. 25(40):9096-9101 (2005).

Chen, Guiquan et al, "A learning deficit related to age and β-amyloid plaques in a mouse model of Alzheimer's disease," *Nature*, vol. 408:975-979 (2000).

Games, Dora et al, "Prevention and Reduction of AD-type Pathology in PDAPP Mice Immunized with $A\beta_{1-42}$," *Ann. NY Acad. Sci.*, vol. 920:274-284 (2000).

Hardy, John, "Amyloid, the presenilins and Alzheimer's disease," *Trends Neurosci.*, vol. 20:154-159 (1997).

Harris, Reed J., "Processing of C-terminal lysine and arginine residues of proteins isolated from mammalian cell culture," *Journal of Chromatography A*, vol. 705:129-134 (1995).

Johnson-Wood, K. et al, "Amyloid precursor protein processing and $A\beta_{42}$ deposition in a transgenic mouse model of Alzheimer's disease," *Proc. Natl. Acad. Sci. USA*, vol. 94:1550-1555 (1997).

Kajkowski, Eileen M. et al, "β-Amyloid Peptide-induced Apoptosis Regulated by a Novel Protein Containing a G Protein Activation Module," *The Journal of Biological Chemistry*, vol. 276(22):18748-18756 (2001).

Koh, Jae-young et al, "β-Amyloid protein increases the vulnerability of cultured cortical neurons to excitotoxic damage," *Brain Research*, vol. 533:315-320 (1990).

Köhler, G. et al, "Continuous cultures of fused cells secreting antibody of predefined specificity," *Nature*, vol. 256:495-497 (1975).

Kostelny, Sheri A. et al, "Formation of a Bispecific Antibody by the Use of Leucine Zippers," *The Journal of Immunology*, vol. 148:1547-1553 (1992).

Lorenzo, A. et al, "Amyloid Fibril Toxicity in Alzheimer's Disease and Diabetes," *Ann. NY Acad. Sci.*, vol. 777:89-95 (1996).

Mattson, Mark P. et al, "β-Amyloid Peptides Destabilize Calcium Homeostasis and Render Human Cortical Neurons Vulnerable to Excitotoxicity," *The Journal of Neuroscience*, vol. 12(2):376-389 (1992).

Selkoe, Dennis J., "Amyloid β Protein Precursor and the Pathogenesis of Alzheimer's Disease," *Cell*, vol. 58:611-612 (1989).

Songsivilai, S. et al, "Bispecific antibody: a tool for diagnosis and treatment of disease," *Clin. exp. Immunol.*, vol. 79:315-321 (1990).

Walsh, Dominic M. et al, "Naturally secreted oligomers of amyloid β protein potently inhibit hippocampal long-term potentiation in vivo," *Nature*, vol. 416:535-539 (2002).

Zameer, Andleeb et al, "Single Chain Fv Antibodies against 25-35 Peptide Fragment of Amyloid-β: Potential Therapeutic for Alzheimers Disease," *Therapeutics and Therapeutic Strategies*, Poster Session P4-420, p. S593.

International Preliminary Report on Patentability for Application No. PCT/US2006/024026, dated Dec. 17, 2007.

PCT Search Report of Dec. 29, 2006 for application PCT/US2006/024026.

Q Sepharose Product Instructions [online], [retrieved on Jun. 11, 2007] Retrieved from http://www6.gelifesciences.com/aptrixiupp00919.nsf/Content/549194A300280337C1256EB40044A91A/$file/71712800AE.pdf Published Amersham Biosciences, 2002.

U.S. Appl. No. 11/454,772, Office Action mailed Mar. 17, 2009.

U.S. Appl. No. 11/454,772, Office Action mailed Jul. 22, 2008.

U.S. Appl. No. 11/454,772, Office Action mailed Dec. 21, 2007.

U.S. Appl. No. 11/454,772, Office Action mailed Jun. 27, 2007.

U.S. Appl. No. 11/454,772, Office Action mailed Feb. 27, 2007.

U.S. Appl. No. 11/454,772, Non-Final Office Action mailed Dec. 15, 2009.

U.S. Appl. No. 11/454,772, Advisory Action mailed Jul. 24, 2009.

* cited by examiner

_US 7,820,799 B2_

METHODS OF PURIFYING FC REGION CONTAINING PROTEINS

RELATED APPLICATIONS

This application claims priority to provisional patent application "METHODS OF PURIFYING Fc REGION CONTAINING PROTEINS", filed Jun. 17, 2005 having Ser. No. 60/691,821. The entire content of this application is incorporated herein.

BACKGROUND OF THE INVENTION

Antibodies are powerful components of the immune system of many animals and especially humans. Recent advances in recombinant technology have allowed for the production of antibodies against virtually any target, for example, cancer cells, bacteria, and viruses. Typically, an antibody is produced using a cell line that has been engineered to express the antibody at high levels. The engineered cell line is subsequently grown in a culture that comprises a complex mixture of sugars, amino acids, and growth factors, as well as various proteins, including for example, serum proteins. However, separation of complete antibodies from cell by-products and culture components to a purity sufficient for use in research or as therapeutics poses a formidable challenge. The purification of the antibody molecules is especially critical if the antibodies are to be used as a drug for administration to humans.

Traditional antibody purification schemes (or trains) often comprise a chromatography step which exploits an ability of the antibody molecule to preferentially bind or be retained by the solid phase (or functionalized solid phase) of a chromatography column compared to the binding or retention of various impurities. Schemes have been proposed or carried out to purify antibodies which first bind CH2/CH3 region-containing proteins to Protein A immobilized on a solid phase, followed by removal of impurities bound to the solid phase by washing the solid phase with a hydrophobic electrolyte solvent and the subsequent recovery of the CH2/CH3 region-containing proteins from the solid phase. However, these schemes are limited in that the conditions used to preferentially bind the CH2/CH3 region-containing proteins also support binding of impurities (e.g., antibodies with incomplete CH2/CH3 regions). In the development of human therapeutics, such impurities are highly undesirable.

Accordingly, a need exists for improvements in the purification of proteins or polypeptides having constant regions, in particular, proteins having Fc regions (e.g., antibodies), produced in cell culture.

SUMMARY OF THE INVENTION

In various aspects, the present invention features methods for separating a protein having an Fc region from a source liquid comprising the protein and one or more impurities. In the methods of the invention, the protein having an Fc region (the target protein) is adsorbed to an Fc binding agent and then the Fc binding agent is washed with a buffer solution containing a divalent cation salt to remove one or more impurities. The protein is then recovered from the Fc binding agent in an elution solution. The methods of the invention are particularly useful for removing impurities such as intron read through variant species (IRT), under disulfide bonded species (UDB) and/or low molecular weight variant species (LMW). The methods of the invention also are effective in removing impurities such as host cell proteins (HCP) and DNA.

The methods of the present invention comprise one or more chromatographic separation steps and in addition can comprise one or more filtration steps. The chromatographic separation steps can be continuous or discontinuous (e.g., a batch approach), or a combination of both. In various embodiments, the methods comprise one or more filtration steps, for example, to remove viruses, concentrate and buffer the solution containing the target protein, and to remove microbial contaminants.

In various embodiments, the Fc region containing protein is an antigen-binding polypeptide (e.g., an antibody or fragment thereof) or an immunoadhesin (e.g., a TNF receptor immunoadhesin). In various embodiments, the Fc region containing protein is an antibody fusion, a murine antibody, a chimeric antibody, or a humanized antibody. In a preferred embodiment, the Fc region containing protein is a human or humanized anti-IL-13 antibody. Alternatively, in other embodiments, the Fc region containing protein can bind an antigen such as Aβ, CD3, CD52, VEGF, EGFR, CD33, CD20, HER-2, TNFα, CD25, RSV, IgE, gp IIb/IIIa, CD11a or α4 integrin In various embodiments, the Fc region containing protein is recombinantly produced. In various embodiments, the Fc region containing protein is recombinantly produced in a Chinese Hamster Ovary (CHO) cell.

In various embodiments, the one or more impurities comprise one or more of a host cell protein, a host cell DNA, a cell culture protein, an undesired species of the protein having an Fc region, and mixtures thereof. For example, in various embodiments the undesired species of the protein having an Fc region comprises one or more of antibody chains or fragments thereof having intron read through sequence, one or more antibody chains or fragments thereof having an improper disulfide linkage, a half-antibody or fragment thereof, a light chain dimer or fragment thereof, and a heavy chain dimer or fragment thereof.

In one aspect, the methods of the present invention purify a protein having an Fc region from a source liquid comprising the protein and one or more impurities by first adsorbing the protein to an Fc binding agent, followed by washing the Fc binding agent with a buffer solution containing a divalent cation salt to remove one or more impurities, and subsequently recovering the protein from the Fc binding agent. In various embodiments, the steps of adsorbing the protein to an Fc binding agent and washing the Fc binding agent with a buffer solution containing a divalent cation salt, are performed at temperature in the range between about 2° C. to about 24° C. In various embodiments, the step of recovering the protein from the Fc binding agent comprises eluting the protein using an elution buffer having a pH in the range from about 2.0 to about 6.5.

In various embodiments, the Fc region binding agent comprises one or more of Protein A and Protein G. In a preferred embodiment, the Fc binding agent is immobilized on a solid phase. This solid phase can comprise, for example, one or more of a bead, an agarose matrix, silica, and mixtures thereof.

The divalent cation salt present in the buffer that is used to wash the Fc binding agent can comprise, for example, a chaotropic salt. Suitable divalent cation salts for preparation of the wash buffer solution include, but are not limited to, magnesium chloride, calcium chloride, nickel chloride and mixtures thereof. In various embodiments, suitable divalent cation salts for preparation of the wash buffer solution include, but are not limited to, thiocyanate ($SCN^-$), perchlorate ($ClO_4^-$), nitrate ($NO_3^-$), chloride, and bromide salts of divalent group II (e.g., magnesium, calcium, barium, etc.)

cations, divalent transition metal (e.g., copper, nickel, manganese, etc.) cations, and combinations of these salts.

In various embodiments, the buffer solution containing the divalent cation salt has a pH value in the range between about 4 to about 9, and in some embodiments, between about 4 to about 8, between about 4.5 to about 7.5 or between about 6 to about 8. Values and ranges included and/or intermediate within the ranges set forth herein are also intended to be within the scope of the present invention. For example, the divalent cation salt has a pH value between about 7.1 to about 7.9, between about 7.2 to about 7.9, between about 7.3 to about 7.7, between about 7.4 to about 7.6, between about 4 to about 5, between about 5 to about 6, between about 6 to about 7, or between about 8 to about 9.

Moreover, ranges having values recited herein as an upper or lower limit are intended to be within the scope of the present invention. For example, the divalent cation salt has a pH of at least about (or about) 4.5, 5, 5.5, 6, 6.5, 7, 7.5, or 8.

In various embodiments, the buffer solution has a divalent cation salt concentration in the range between about 0.1 M to about 5 M, and in some embodiments between about 0.5 M to about 3M, between about 1.0 M to about 3 M or between about 0.6 M to about 2.5 M. For example, the divalent cation buffer may comprise at least about 0.6 M $CaCl_2$ or at least about 2M $MgCl_2$ or at least about 2M $CaCl_2$. Values and ranges included and/or intermediate within the ranges set forth herein are also intended to be within the scope of the present invention. For example, the buffer solution has a divalent cation salt concentration between about 0.5 M to about 0.75 M, between about 0.5 M to about 0.8 M, between about 0.5 M to about 0.9 M, between about 0.5 M to 1.0 M, between about 0.5 M to 2 M, between about 1.5 M to about 2.0 M, between about 1.5 M to about 2.5 M, between about 1.5 M to about 3.0 M, or between about 2.5 M to about 3 M.

Moreover, ranges having values recited herein as an upper or lower limit are intended to be within the scope of the present invention. For example, the buffer solution has a divalent cation salt concentration of at least about (or about) 0.6 M, 1 M, 1.5 M, 2 M, 2.5 M, or 3 M. In various embodiments, the buffer solution containing a divalent cation salt has a temperature in the range between about 2° C. to about 24° C.

In various embodiments, the step of recovering the protein from the Fc binding agent comprises eluting the protein using an elution buffer having a pH in the range of about 2.0 to about 6.5, preferably in the range of about 2.0 to about 4.0, more preferably in the range of about 2.5 to about 3.5. Values and ranges included and/or intermediate within the ranges set forth herein are also intended to be within the scope of the present invention. For example, the elution buffer has a pH of between about 2 to about 3 or between about 3 to about 4.

Moreover, ranges having values recited herein as an upper or lower limit are intended to be within the scope of the present invention. For example, the elution buffer has a pH of at least about (or about) 2, 2.5, 3, 3.5 or 4.

In various embodiments, the recovered proteins can be subjected to additional purification steps either prior to, or after, the Fc binding agent chromatography step. For example, exemplary further purification steps include, but are not limited to: anion exchange chromatography, cation exchange chromatography, immobilized metal affinity chromatography, hydrophobic interaction chromatography (HIC), hydroxyapatite chromatography, dialysis, affinity chromatography, ammonium sulphate precipitation, ethanol precipitation, reverse phase HPLC (RP-HPLC), chromatofocusing, ultrafiltration, diafiltration, microfiltration, and gel filtration. In various embodiments, the Fc binding agent chromatography step is followed by an anion exchange chromatography and a HIC step. In various embodiments, the chromatography steps are further followed by a virus filtration step, an ultrafiltration/diafiltration step, and/or a microbial contaminant filtration step.

In one aspect, the present invention provides methods for purifying an antibody from an impurity-containing solution thereof. In various embodiments, the methods comprise first adsorbing the protein to an Fc binding agent, followed by washing the Fc binding agent with a buffer solution containing a divalent cation salt to remove one or more impurities, and subsequently recovering the protein from the Fc binding agent to produce a first eluent pool.

In various embodiments, the purification process continues with subjecting the first eluent pool to ion exchange chromatography by contacting an ion exchange resin with the first eluent pool such that the target protein does not adsorb to the resin and recovering the flow-through target protein to produce a second eluent pool. In various embodiments, the ion exchange chromatography step further comprises washing the ion exchange resin with a buffered wash solution to recover at least a portion of any adsorbed target protein.

In various embodiments, the purification process continues with subjecting the second eluent pool to hydrophobic interaction chromatography by adsorbing the target protein to a hydrophobic interaction resin (e.g., a solid phase functionalized with hydrophobic ligands), washing the hydrophobic interaction resin with a buffered wash solution with an ionic strength which does not substantially elute the target protein, and recovering the purified target protein (typically using an elution buffer with an ionic strength low enough to desorb the target protein from the hydrophobic interaction resin).

In preferred embodiments of the various aspects of the inventions, the Fc binding agent is immobilized on a solid phase, which is preferably equilibrated with a suitable buffer prior to contact with the source liquid. The solid phase is preferably a column comprising agarose immobilizing the Fc binding agent. In various embodiments, the column is coated with a reagent, such as glycerol, to decrease or prevent non-specific adherence to the column.

In various embodiments, the proteins purified by methods of the present invention can be formulated in a pharmaceutically acceptable carrier and used for various diagnostic, therapeutic or other uses known for such molecules.

In various aspects, the present invention provides methods for purifying an Fc region containing protein from a solution containing the protein and intron read-through variants (IRT) thereof. In featured aspects, methods of the present invention are used to reduce the levels of one or more intron read-through variant species in a protein preparation, for example, in an antibody preparation. In various embodiments, the protein recovered from the Fc binding agent has a level of intron read-through variants that is at least 5 fold less than the level of intron read-through variants in the source liquid, and in some embodiments at least 10 fold less than the level of intron read-through variants in the source liquid. In various embodiments, the intron read-through variants comprise less than about 1.0%, 0.8%, 0.5%, 0.2% or 0.1% of the species of said protein in the solution containing said protein recovered from the Fc binding agent.

In various aspects, the present invention provides methods for purifying an Fc region containing protein from a solution containing the protein and low molecular weight variants (LMW) thereof. In featured aspects, methods of the present invention are used to reduce the levels of one or more low molecular weight variant species in a protein preparation, for example, in an antibody preparation. In various embodiments, the protein recovered from the Fc binding agent has a level of low molecular weight variants that is at least 5 fold less than the level of low molecular weight variants in the source liquid, and in some embodiments at least 10 fold less than the level of low molecular weight variants in the source liquid. In various embodiments, the low molecular weight variants comprise less than about 1.0%, 0.8%, 0.5%, 0.2% or 0.1% of the species of said protein in the solution containing said protein recovered from the Fc binding agent.

In various aspects, the present invention provides methods for purifying an Fc region containing protein from a solution containing the protein and under disulfide bonded variants (UDB) thereof. In featured aspects, methods of the present invention are used to reduce the levels of one or more under disulfide bonded variant species in a protein preparation, for example, in an antibody preparation. In various embodiments, the protein recovered from the Fc binding agent has a level of under disulfide bonded variants that is at least 5 fold less than the level of under disulfide bonded variants in the source liquid, and in some embodiments at least 10 fold less than the level of under disulfide bonded variants in the source liquid. In various embodiments, the under disulfide bonded variants comprise less than about 20%, 15%, 10%, 5%, 2%, or 1% of the species of said protein in the solution containing said protein recovered from the Fc binding agent.

In another aspect, the invention pertains to an Fc region containing protein purified according to the method of invention.

In another aspect, the present invention provides a system suitable for performing any of the methods that comprise at least the steps of first adsorbing the protein to an Fc binding agent, followed by washing the Fc binding agent with a buffer solution containing a divalent cation salt to remove one or more impurities, and subsequently recovering the protein from the Fc binding agent.

In another aspects, the present invention provides a purification train for performing any of the methods that comprise at least the steps of first adsorbing the protein to an Fc binding agent, followed by washing the Fc binding agent with a buffer solution containing a divalent cation salt to remove one or more impurities, and subsequently recovering the protein from the Fc binding agent.

The present invention also features, in various aspects, kits for use in performing one or more of the methods of the present invention. In various embodiments, the kit comprises at least one reagent and instructions for use of the kit. For example, a kit can comprise one or more reagents such as an Fc binding agent, a divalent cation salt and reagents for the preparation of buffer wash solution containing a divalent cation salt, along with instructions for use of the kit.

DETAILED DESCRIPTION OF THE INVENTION

Prior to further describing the invention, it may be helpful to an understanding thereof to set forth definitions of certain terms to be used herein. The definitions set forth herein have been grouped for ease of reference only and not by way of limitation.

Protein Related Definitions

In various aspects, the present invention provides methods for purifying an Fc region containing protein from a solution containing the protein and one or more read-through variants thereof, such as, for example, intron read-through variants. In featured aspects, methods of the present invention are used to reduce the levels of one or more intron read-through (IRT) variant species in a protein preparation, for example, in an antibody preparation. The terms "intron read-through variant," and "intron read-through variant species" are used interchangeably herein and refer to the product of a process where in the synthesis of the Fc region containing protein of interest (e.g., the target protein) polypeptide chain elongation is terminated prior to transcription of a coding region by a stop codon in the intron prior to the coding region. The result is a variant of the protein of interest (i.e., an intron read-through variant) with one or more incomplete or missing domains. Such introns can contain more than one stop codon resulting in the possibility of producing several different intron read-through variants.

The term "under disulfide bonded variant" or "UDB" refers to any species where at least one disulfide bond is missing. The missing disulfide bond can be either an interchain disulfide bond or an intrachain disulfide bond or a combination of the two.

The term "low molecular weight species" or "LMW" species refers to variants of the Fc region containing protein including a protein species that consists of free heavy chain, free light chain, IRT species, half-molecule, and three-quarters-molecule, or mixtures thereof.

Protein A is an about 42 kD cell wall protein found in most strains of *Staphylococcus aureas* which binds with high affinity (about $10^{-8}$ M to human IgG) to the Fc region of antibodies. As used herein, the term "Protein A" encompasses Protein A recovered from a native source thereof, Protein A produced synthetically (e.g. by peptide synthesis, by recombinant techniques, etc.), and variants thereof which retain the ability to bind proteins which have a CH2/CH3 region.

Protein G is a cell wall protein from group G streptococci. Protein G is a type III Fc-receptor which binds with high affinity to the Fc region of antibodies, in particular, IgG antibodies. As used herein, the term "Protein G" encompasses Protein G recovered from a native source thereof, Protein G produced synthetically (e.g., by peptide synthesis, by recombinant techniques, etc.), and variants thereof, which retain the ability to bind proteins which have an Fc region.

The term "antibody" or "immunoglobulin" (used interchangeably herein) refers to an antigen-binding protein having a basic four-polypeptide chain structure consisting of two heavy and two light chains, said chains being stabilized, for example, by interchain disulfide bonds, which has the ability to specifically bind antigen. Both heavy and light chains are folded into domains.

The term "domain" refers to a globular region of a heavy or light chain polypeptide comprising peptide loops (e.g., comprising 3 to 4 peptide loops) stabilized, for example, by β-pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. "Constant" domains on the light chain are referred to interchangeably as "light chain constant regions", "light chain constant domains", "CL" regions or "CL" domains). "Constant" domains on the heavy chain are referred to interchangeably as "heavy chain constant regions", "heavy chain constant domains", "CH" regions or "CH" domains). "Variable" domains on the light chain are referred to interchangeably as "light chain variable regions", "light chain variable domains", "VL" regions or "VL" domains). "Variable" domains on the heavy chain are referred to interchangeably as "heavy chain variable regions", "heavy chain variable domains", "VH" regions or "VH" domains).

The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab')2, Fabc and/or Fv fragments. The term "antigen-binding fragment" refers to a polypeptide fragment of an immunoglobulin or antibody that binds antigen or competes with the intact antibody from which they were derived for specific antigen binding.

The terms "antibody fusion protein" and "antibody fusion" refers to a fusion protein including all or a portion of an antibody fused to at least one non-antibody protein portion or polypeptide. Fusion is generally accomplished by genetic engineering of the gene encoding said protein. Additional exemplary antibody fusion proteins include the cell receptor binding portion of an antibody (including the Fc region) fused to all or a portion of another soluble or cellular biological protein, for example a receptor (cellular or soluble) or portion thereof, a cytokine or portion thereof, an enzyme or portion thereof, etc. Such antibody fusion proteins that comprise the Fc region of the antibody fused to another protein are also referred to in the art as Fc fusion proteins.

The term "Fc binding agent" refers to a molecule that is capable of binding to the Fc region of an antibody (e.g., an IgG antibody) including, but not limited to, a complement protein, an Fc receptor or a bacterial-derived protein, such as Protein A or Protein G, that has high affinity for the Fc region of an antibody.

The term "Fc region" refers to a C-terminal region of an IgG antibody, in particular, the C-terminal region of the heavy chain(s) of said IgG antibody. Although the boundaries of the Fc region of an IgG heavy chain can vary slightly, a Fc region is typically defined as spanning from about amino acid residue Cys226 to the carboxyl-terminus of an IgG heavy chain(s).

Chromatography Related Definitions

The term "source liquid", as used herein, refers to a liquid containing at least one target substance which is sought to be purified from other substances also present. Source liquids can, for example, be aqueous solutions, organic solvent systems, or aqueous/organic solvent mixtures or solutions. The source liquids are often complex mixtures or solutions containing many biological molecules (such as proteins, antibodies, hormones, and viruses), small molecules (such as salts, sugars, lipids, etc.) and even particulate matter. While a typical source liquid of biological origin may begin as an aqueous solution or suspension, it may also contain organic solvents used in earlier separation steps such as solvent precipitations, extractions, and the like. Examples of source liquids that may contain valuable biological substances amenable to the purification by various embodiments the present invention include, but are not limited to, a culture supernatant from a bioreactor, a homogenized cell suspension, plasma, plasma fractions, and milk.

The term "target substance" or "target protein" refers herein to the one or more desired Fc region containing proteins to be purified from the source liquid. The target substance may be present in the source liquid as a suspension or in solution.

The term "impurities" refers to materials in the source liquid that are different from the target substance(s) and are desirably excluded from the final target substance product(s). Typical impurities include nucleic acids, proteins (including intron-read-through species, low molecular weight species and under disulfide bonded species), peptides, endotoxins, viruses and small molecules.

As used herein, the term "solid phase" refers to a non-aqueous matrix with which a target substance interacts during purification or to which an Fc binding agent can adhere. Suitable solid phase materials include, but are not limited to, glass, silica (e.g. silica gel), polysaccharides (e.g., a polysaccharide matrix) such as agarose and cellulose, organic polymers such as polyacrylamide, methylmethacrylate, and polystyrene-divinylbenzene copolymers such as for example Amberlite™ resin, (commercially available from Rohm & Haas Chemical Co., Philadelphia, Pa.). The solid phase can be selected from any of the groups of resins commonly described as affinity, ion exchange and ion capture resins. The solid phase can be, for example, a purification column, a discontinuous phase of discrete particles, or a combination thereof. The solid phase can be of porous or nonporous character, and can be compressible or incompressible. In various embodiments, the solid phase is a polymeric matrix or an agarose particle or bead. In various embodiments, the solid phase can be coated with a reagent (such as glycerol), for example, to prevent nonspecific adherence of impurities to the solid phase. An Fc binding solid phase need only possess a chemistry or an associated ligand that will permit Fc binding agent to adhere to the surface of the solid phase. Preferred solid phase materials will be physically and chemically resilient to the conditions employed in the purification process including pumping and cross-flow filtration, and temperatures, pH, and other aspects of the liquids employed.

"Affinity ligand" refers to a moiety that binds selectively or preferentially to a component of the source liquid through a specific interaction with a binding site of the component. In the present invention, the affinity ligand (e.g., an Fc binding agent) is typically immobilized to a solid phase such as a resin. Examples of affinity ligands that can be bound to the resin support to provide chromatography resins useful in the process of the present invention include, but are not limited to, Protein A, Protein G, and their analogs, which selectively bind to a protein Fc region. Methods of binding affinity ligands to solid support materials are well known in the purification art. See, e.g., the reference texts Affinity Separations: A Practical Approach (Practical Approach Series), Paul Matejtschuk (Editor), Irl Pr: 1997; and Affinity Chromatography, Herbert Schott, Marcel Dekker, New York: 1997.

"Affinity chromatography resin" or "affinity resin" refers to a chromatography resin that comprises a solid phase or substrate with affinity ligands bound to its surfaces.

"Ion exchange chromatography resin" or "ion exchange resin" refers to a solid support to which are covalently bound ligands that bear a positive or negative charge, and which thus has free counterions available for exchange with ions in a solution with which the ion exchange resin is contacted.

"Cation exchange resins" refers to an ion exchange resin with covalently bound negatively charged ligands, and which thus has free cations for exchange with cations in a solution with which the resin is contacted. A wide variety of cation exchange resins are known in the art, for example, those wherein the covalently bound groups are carboxylate or sulfonate. Commercially available cation exchange resins include CMC-cellulose, SP-Sephadex™, and Fast S-Sepharose™ (the latter two being commercially available from Pharmacia).

"Anion exchange resins" refers to an ion exchange resin with covalently bound positively charged groups, such as quaternary amino groups. Commercially available anion exchange resins include DEAE cellulose, TMAE, QAE Sephadex™, and Fast Q Sepharose™ (the latter two being commercially available from Pharmacia).

As used herein, the term "chaotropic salt" refers to a salt which comprises one or more ionic components that are low in the lyotropic series that are able to penetrate protein hydration shells and bind directly to their surfaces. This disrupts cohydrative association, favoring protein solubilization. Examples of chaotropic salts include, but are not limited to, halide salts of the Group II elements (e.g., calcium chloride, magnesium chloride, barium chloride, calcium bromide, magnesium bromide, barium bromide, calcium iodide, magnesium iodide, barium iodide).

Examples of suitable divalent cations salts include, but are not limited to, salts of $Mn^{2+}$, $Ni^{2+}$ or $Cu^{2+}$, $Mg^{2+}$, $Ca^{2+}$ and $Ba^{2+}$ with thiocyanate ($SCN^-$), perchlorate ($ClO_4^-$), nitrate ($NO_3^-$), chloride ($Cl^-$), and bromide ($Br^-$); and combinations thereof.

In certain embodiments, the divalent cation salt comprises a divalent cation (e.g., $Mg^{2+}$, $Ca^{2+}$, $Ni^{2+}$ or $Ba^{2+}$). Preferred chaotropic salts for use in the featured processes are $MgCl_2$, $NiCl_2$ and $CaCl_2$. After the divalent cation salt wash step, the target protein is eluted from the affinity chromatography matrix.

A "buffer" is a substance which, by its presence in solution, increases the amount of acid or alkali that must be added to cause unit change in pH. A buffered solution resists changes in pH by the action of its acid-base conjugate components. Buffered solutions for use with biological reagents are generally capable of maintaining a constant concentration of hydrogen ions such that the pH of the solution is within a physiological range. The term "physiological pH" refers to the pH of mammalian blood (i.e., 7.38 or about 7.4). Thus a physiologic pH range is from about 7.2 to 7.6. Traditional buffer components include, but are not limited to, organic and inorganic salts, acids and bases. Exemplary buffers for use in purification of biological molecules (e.g., protein molecules) include the zwitterionic or "Good" Buffers, see e.g., Good et al. (1966) *Biochemistry* 5:467 and Good and Izawa (1972) *Methods Enzymol.* 24:62. Exemplary buffers include but are not limited to TES, MES, PIPES, HEPES, MOPS, MOPSO, TRICINE and BICINE.

The "equilibration buffer" herein is a buffer used to prepare the Fc binding reagent, solid phase, or both, for loading of the source liquid containing the target protein. The equilibration buffer is preferably isotonic and commonly has a pH in the range from about 6 to about 8. The "loading buffer" is a buffer used to load the source liquid containing the Fc region containing protein and impurities onto the solid phase to which the Fc binding agent is immobilized. Often, the equilibration and loading buffers are the same. The "elution buffer" is used to elute the Fc region-containing protein from the immobilized Fc binding agent. Preferably the elution buffer has a low pH and thereby disrupts interactions between the Fc binding agent and the protein of interest. Preferably, the low pH elution buffer has a pH in the range from about 2 to about 5, most preferably in the range from about 3 to about 4. Examples of buffers that will control the pH within this range include glycine, phosphate, acetate, citrate and ammonium buffers, as well as combinations of these. The preferred such buffers are citrate and acetate buffers, most preferably sodium citrate or sodium acetate buffers. Other elution buffers are contemplated including high pH buffers (e.g. those having a pH of 9 or more) or buffers comprising a compound or composition such as $MgCl_2$ (2 mM) for eluting the protein of interest.

"Wash liquid" or "wash buffer" as used herein all refer herein to the liquid used to carry away impurities from the chromatography resin to which is bound the target substance. More than one wash liquid can be employed sequentially, e.g., with the successive wash liquids having varying properties such as pH, conductivity, solvent concentration, etc., designed to dissociate and remove varying types of impurities that are non-specifically associated with the chromatography resin.

"Elution liquid" or "elution buffer" refers herein to the liquid that is used to dissociate the target substance from the chromatography resin after it has been washed with one or more wash liquids. The elution liquid acts to dissociate the target substance without denaturing it irreversibly. Typical elution liquids are well known in the chromatography art and may have higher concentrations of salts, free affinity ligands or analogs, or other substances that promote dissociation of the target substance from the chromatography resin. "Elution conditions" refers to process conditions imposed on the target substance-bound chromatography resin that dissociate the target substance from the chromatography resin, such as the contacting of the target substance-bound chromatography resin with an elution liquid or elution buffer to produce such dissociation.

"Cleaning liquid" or "cleaning buffer" refers herein to the liquid that is used to wash the chromatography resin after the completion of the purification process. The cleaning liquid may contain a detergent, a virus-inactivating agent, or relatively high concentrations of salts, and may have a higher or lower pH than the liquids used during the purification process. Its purpose is to decontaminate the chromatography resin to render it ready for reuse. Typical cleaning liquids are well-known in the chromatography art.

"Storage liquid" or "storage buffer" refers herein to the liquid in which the chromatography resin is suspended between uses. Storage liquids, in addition to buffering ions, may also contain microbicides or other preservatives. Such storage liquids are well known in the chromatography art.

In various aspects, the present invention features methods for purifying a protein having an Fc region from a source liquid comprising the protein and one or more impurities by adsorbing the protein to an Fc binding agent, followed by washing the Fc binding agent with a buffer solution containing a divalent cation salt to remove one or more impurities, and subsequently recovering the protein from the Fc binding agent. Suitable Fc binding agents include, but are not limited to, Protein A and Protein G.

The present invention features processes for the purification of Fc region containing proteins, for example, antibodies. Exemplary purification processes include an affinity chromatography step. The affinity chromatography step can be continuous, discontinuous, or a combination of both. For example, the affinity chromatography step can be performed as a discontinuous process, such as, for example, a batch process. Affinity chromatography is the process of bioselective adsorption and subsequent recovery of a target compound from an immobilized ligand. This process allows for the highly specific and efficient purification of the target compound. The process requires the utilization of an appropriately selective ligand (e.g., Fc binding agent) which will bind the target compound (e.g., Fc region containing protein) generally with a dissociation constant in the range of $10^{-4}$ to $10^{-8}$, while permitting recovery under mild conditions. The ligand is generally immobilized on a beaded and porous matrix which may be in the form of a column packing or batchwise adsorption medium.

A preferred binding agent is Protein A. Protein A binds the Fc region of immunoglobulins. Protein A consists of six regions, five of which bind IgG. It binds with high affinity to human $IgG_1$, $IgG_2$ and $IgG_4$, as well as mouse $IgG_{2a}$, $IgG_{2b}$ and $IgG_3$. Protein A binds with moderate affinity to human IgD, IgM, IgA and IgE as well as mouse $IgG_1$. As an affinity ligand, Protein A is immobilized to a matrix so that these regions are free to bind. One molecule of immobilized Protein A can bind at least two molecules of IgG. Native and recombinant versions of Protein A share similar specificity for the Fc region of IgG. Recombinant Protein A (rprotein A) can be engineered to include, for example, a C-terminal cysteine, and can be immobilized via thioetser coupling to a solid phase matrix. Such coupling results in enhanced binding capacity of the protein A.

An alternative binding agent is Protein G. Protein G is specific for IgG, binding with high affinity for human $IgG_1$, $IgG_2$, $IgG_3$ and $IgG_4$, as well as mouse $IgG_1$ and $IgG_3$. Protein G PLUS has moderate affinity for human $IgG_4$ and mouse $IgG_{2a}$, $IgG_{2b}$ and $IgG_3$. Recombinant protein G (rProteinG) can be engineered to delete the albumin-binding region of the native protein. Recombinant Protein G contains two Fc binding regions.

An alternative binding agent is Protein A/G. Protein A/G is a genetically-engineered protein that combines the IgG binding profiles of both Protein A and Protein G. It is a gene fusion product secreted from a nonpathogenic form of *Bacillus*. Protein A/G contains four Fc binding domains from Protein A and two from Protein G. Protein A/G is not as pH dependent as Protein A, but otherwise has the additive properties of Protein A and G.

Protein A/G binds to all human IgG subclasses, particularly suitable for purification of polyclonal or monoclonal IgG antibodies whose subclasses have not been determined. In addition, it binds to IgA, IgE, IgM and (to a lesser extent) IgD. Protein A/G also binds well to all mouse IgG subclasses, particularly suitable for purification of mouse monoclonal antibodies from IgG subclasses, without interference from IgA, IgM and murine serum albumin. (See e.g., Sikkema. (1989) *Amer. Biotech. Lab* 7, 42.) Individual subclasses of mouse monoclonals can have a stronger affinity for the chimeric Protein A/G than to either Protein A or Protein G. (See e.g., Eliasson et al. (1988) *J. Biol. Chem.* 263, 4323-4327.)

In the present invention, the immobilized Fc binding agent (e.g., Protein A) is washed with a divalent cation salt solution to remove impurities. In particular, it has been discovered that undesirable impurities produced as a result of recombinant antibody expression technologies can be removed using a divalent cation salt wash step.

The methods of the present invention can optionally include purification steps subsequent to the affinity chromatography and divalent cation wash step. Subsequent purification steps can include an ion exchange chromatography step and/or a hydrophobic interaction chromatography (HIC) step. Subsequent chromatography steps can be continuous, discontinuous (e.g., such as a batch process), or a combination of both. Ion exchange chromatography separates molecules based on differences between the overall charge of the proteins. The target protein must have a charge opposite that of the functional group attached to the resin in order to bind. For example, antibodies, which generally have an overall positive charge, will bind well to cation exchangers, which contain negatively charged functional groups. Because this interaction is ionic, binding must take place under low ionic conditions. Elution is achieved by increasing the ionic strength to break up the ionic interaction, or by changing the pH of the protein.

Whereas ion exchange chromatography relies on the charges of proteins to isolate them, hydrophobic interaction chromatography uses the hydrophobic properties of some proteins. Hydrophobic groups on the protein bind to hydrophilic groups on the column. The more hydrophobic a protein is, the stronger it will bind to the column. The HIC step removes, for example, host cell derived impurities (e.g., DNA and other high and low molecular weight product-related species). Further purification steps can include virus removing steps as well as ultrafiltration and/or diafiltration steps, as described herein.

In various embodiments, the Fc region containing protein is an antibody or an antibody fusion protein having an Fc region that binds to an Fc receptor of the Fc binding agent. The use of the buffer solution containing a divalent cation salt to wash the Fc binding agent allows for greater removal of impurities, such as, for example, read-through variants and constant region containing fragments (including LMW and UDB species), of the protein of interest (e.g., the target substance in the source liquid).

The methods of the present invention comprise one or more chromatographic separation steps and in addition can comprise one or more filtration steps for separating a protein having an Fc region ("the target protein") from impurities in a source liquid. For example, the source liquid may be filtered, centrifuged or otherwise processed to remove particulate debris and the like before contacting the source liquid with the Fc binding agent. For example, using recombinant techniques, proteins can be produced intracellularly, in the periplasmic space, or secreted directly into the culture medium. If the protein is produced intracellularly, the particulate debris, either host cells or lysed fragments, can be removed, for example, by centrifugation or ultrafiltration. Where the protein is secreted into the medium, the recombinant host cells can be separated from the cell culture medium, for example, by tangential flow filtration.

In various embodiments, the source liquid containing the target protein is contacted with an Fc binding agent (preferably immobilized on a solid phase and equilibrated with a suitable buffer) such that the target protein adsorbs to the Fc binding agent (e.g., an immobilized Fc binding agent). The source liquid is contacted with the Fc binding agent (e.g., an immobilized Fc binding agent) in a loading buffer which may be the same as the equilibration buffer. As the impurity-containing source liquid flows through the solid phase, the target protein is adsorbed to the Fc binding agent and various other impurities (such as host cell proteins, where the target protein is produced in a recombinant host cell, or other process-derived impurities) flow-through or bind nonspecifically to the solid phase. In various embodiments, the Fc binding agent is Protein A, and the equilibration buffer can be 20 mM Tris, 0.15 M NaCl, pH 7.5. Other suitable equilibration buffers include, for example, BIS, HEPES, etc., at physiological concentrations, for example, concentration in the range between about 0.5 mM and about 100 mM (e.g., 10 mM, 20 mM, 50 mM, etc.), and physiological salt concentrations (e.g., about 0.15 mM NaCl), and at pH from 5.0-9.0.

The solid phase is preferably an agarose (e.g., Sepharose) bead or particle for immobilizing the Fc binding agent. In various embodiments, the column is coated with a reagent, such as glycerol, to decrease or prevent nonspecific adherence to the column. In various embodiments, the Fc binding agent is Protein A. The rmp Protein A Sepharose™ Fast Flow (FF) column, commercially available from Amersham Biosciences, is an example of a suitable Protein A column for use in the featured methodologies.

The Fc binding agent is then washed with a buffered wash solution containing a divalent cation salt to remove protein variant species bound to the solid phase or Fc binding agent. In particular, it has been discovered that the use of a divalent cation salt wash step can remove a significant amount of undesirable impurities. Specifically, it has been discovered that intron read-through variants, low molecular weight variants and under-disulfide bonded variants of a target protein can be removed using a divalent cation salt wash. Moreover, host cell proteins (HCP) and DNA also can be removed using the divalent cation salt wash. In various embodiments, the divalent cation salt in the wash solution contains a chaotropic salt. Examples of suitable chaotropic salts include, but are not limited to, calcium chloride ($CaCl_2$), nickel chloride ($NiCl_2$) and magnesium chloride ($MgCl_2$). While a single divalent cation salt can be present in the wash solution, in various embodiments, two or more divalent cation salts can be used.

In various embodiments, wash solutions in addition to the divalent cation salt containing wash solution are used to remove impurities. For example, in various embodiments a 20 to 50 mM Tris, 0.75 to 2.0 M NaCl, pH 5.0-9.0 solution, and/or a 10 mM Tris, pH 7.5 solution are used to wash the Fc binding agent prior to, after, or both prior to and after, washing Fc binding agent with the divalent cation salt containing wash solution.

In various embodiments, the divalent cation salt is preferably added at a concentration between about 0.5 M and about 2.5 M to a pH buffered solution having a pH in the range from about 5 to about 9, and preferably a pH in the range from about 7 to about 8. Preferred concentrations of the divalent cation salt include, but are not limited to, 0.6 M, 2.0 M and 2.5 M. Suitable buffers for this purpose include, but are not limited to, Tris or acetate buffers in a concentration from 20 to 50 mM.

Following the washing step(s), the target protein is recovered from the Fc binding agent. This is normally achieved using a suitable elution buffer. The target protein can, for example, be eluted from the column using an elution buffer having a low pH, e.g. in the range from about 2 to about 6.5, and preferably in the range from about 2.5 to about 3.5.

In various embodiments, the target protein thus recovered can be formulated in a pharmaceutically acceptable carrier and used for various diagnostic, therapeutic or other uses known for such molecules.

In various embodiments, the eluted target protein preparation can be subjected to additional purification steps after the Fc binding agent chromatography step. For example, exemplary further purification steps include, but are not limited to: anion exchange chromatography, cation exchange chromatography, hydrophobic interaction chromatography (HIC), hydroxyapatite chromatography, dialysis, affinity chromatography (including immobilized metal affinity chromatography), size exclusion chromatography (SEC), ammonium sulphate precipitation, ethanol precipitation, reverse phase HPLC (RP-HPLC), chromatofocusing, ultrafiltration, diafiltration, and gel filtration. In various embodiments, the Fc binding agent chromatography step is followed by an anion exchange chromatography and a HIC step. In various embodiments, the chromatography steps are further followed by a virus filtration step, an ultrafiltration/diafiltration step, and a microbial contaminant filtration step. In various embodiments, these additional purification steps may be conducted prior to the Fc binding agent chromatography step. In various aspects, the methods herein involve purifying an Fc region-containing protein from impurities by Protein A chromatography.

In various embodiments, methods for purification of an Fc region containing protein (the target protein) begin with adsorbing the target protein to an Fc binding agent comprising Protein A immobilized on a solid phase, followed by washing the Fc binding agent with a buffer solution containing a divalent cation salt to remove one or more impurities, and subsequently recovering the protein from the Protein A to produce a first eluent pool.

In various embodiments, the purification process continues with subjecting the first eluent pool to anion exchange chromatography by contacting an anion exchange resin with the first eluent pool such that impurities adsorb to the resin, while the target protein does not adsorb to the resin. Thus, the target protein can be recovered from the flow-through to produce a second eluent pool. In various embodiments, the anion exchange chromatography step further comprises washing the anion exchange resin with a buffered wash solution to recover at least a portion of the adsorbed target protein, which would then be combined with the second eluent pool. Alternatively, the first eluent pool may be contacted with the anion exchange resin in such a way that the antibody adsorbs, allowing any impurities to flow-through, optionally followed by washing and eluting the adsorbed antibody.

In various embodiments, the purification process continues with subjecting the second eluent pool to HIC by adsorbing the target protein to a hydrophobic interaction resin (e.g., a solid phase functionalized with hydrophobic ligands), washing the hydrophobic interaction resin with a buffered wash solution with an ionic strength which does not substantially elute the target protein, and recovering the target protein (typically using an elution buffer with an ionic strength low enough to desorb the target protein from the hydrophobic interaction resin) on a third eluent pool. Alternatively, the second eluent pool may be contacted with the HIC column in such a way that the target protein does not adsorb, recovering the flow-through target protein as a third eluent pool.

In various embodiments, the purification process includes one or more filtration steps, for example, to remove viruses, concentrate and buffer the solution containing the target protein, and to remove microbial contaminants.

In various embodiments, the present invention provides methods for the purification of a protein having an Fc region from a source liquid comprising the protein and one or more impurities where the impurities comprise one or more IRT variants. In one embodiment, the methods provide for about a 2 to about a 20 fold reduction in IRT variant levels from those in the source liquid. Preferably, IRT variant levels are reduced by at least 5 fold, and more preferably IRT variant levels are reduced by at least 10 fold. For example, in a source liquid (starting sample) having about 3-5% IRT antibody variants (as a percentage of total species in the source liquid) IRT antibody variant species can be reduced to about 0.3 to about 0.5%. In various embodiments, IRT variant species are reduced to: less than 1%, less than 0.8%, less than 0.5%, less than 0.3%, less than 0.2%, and/or less than 0.1%. Preferably, in the purification of a source liquid for the preparation of a protein, IRT variants are reduced to: less than 1%, less than 0.8%, less than 0.5%, less than 0.3%, less than 0.2%, and/or less than 0.1% as a percentage of total species in the source liquid.

In various embodiments, the present invention provides methods for the purification of a protein having an Fc region from a source liquid comprising the protein and one or more impurities where the impurities comprise one or more LMW variants. In one embodiment, the methods provide for about a 2 to about a 20 fold reduction in LMW variant levels from those in the source liquid. Preferably, LMW variant levels are reduced by at least 5 fold, and more preferably LMW variant levels are reduced by at least 10 fold.

For example, in a source liquid (starting sample) having about 20% UDB antibody variants (as a percentage of total species in the source liquid) UDB antibody variant species can be reduced to about 10% to about 2%. In various embodiments, UDB variant species are reduced to: less than 20%, less than 45%, less than 10%, less than 5%, less than 2%, or less than 1%. Preferably, in the purification of a source liquid for the preparation of a protein, UDB variants are reduced to: less than 20%, less than 15%, less than 10%, less than 5%, less than 2%, or less than 1% as a percentage of total species in the source liquid.

For example, in a source liquid (starting sample) having about 3-5% LMW antibody variants (as a percentage of total species in the source liquid) LMW antibody variant species can be reduced to about 0.3 to about 0.5%. In various embodiments, LMW variant species are reduced to: less than 1%, less than 0.8%, less than 0.5%, less than 0.3%, less than 0.2%, and/or less than 0.1%. Preferably, in the purification of a source liquid for the preparation of a protein, LMW variants are reduced to: less than 1%, less than 0.8%, less than 0.5%, less than 0.3%, less than 0.2%, and/or less than 0.1% as a percentage of total species in the source liquid.

In various embodiments, the present invention provides methods for the purification of a protein having an Fc region from a source liquid comprising the protein and one or more impurities where the impurities comprise one or more UDB variants. In one embodiment, the methods provide for about a 2 to about a 20 fold reduction in UDB variant levels from those in the source liquid. Preferably, UDB variant levels are reduced by at least 5 fold, and more preferably UDB variant levels are reduced by at least 10 fold.

For example, in a source liquid (starting sample) having about 20% UDB antibody variants (as a percentage of total species in the source liquid) UDB antibody variant species can be reduced to about 10% to about 2%. In various embodiments, UDB variant species are reduced to: less than 20%, less than 15%, less than 10%, less than 5%, less than 2%, or less than 1%. Preferably, in the purification of a source liquid for the preparation of a protein, UDB variants are reduced to: less than 20%, less than 15%, less than 10%, less than 5%, less than 2%, or less than 1% as a percentage of total species in the source liquid.

Also, for example, in a source liquid (starting sample) having about 3-5% UDB antibody variants (as a percentage of total species in the source liquid) UDB antibody variant species can be reduced to about 0.3 to about 0.5%. In various embodiments, UDB variant species are reduced to: less than 1%, less than 0.8%, less than 0.5%, less than 0.3%, less than 0.2%, and/or less than 0.1%. Preferably, in the purification of a source liquid for the preparation of a protein, UDB variants are reduced to: less than 1%, less than 0.8%, less than 0.5%, less than 0.3%, less than 0.2%, and/or less than 0.1% as a percentage of total species in the source liquid.

Proteins for Use in the Purification Methods of the Invention

The protein having an Fc region to be purified according to the invention as described herein is prepared using techniques which are well established in the art and include, for example, synthetic techniques (such as recombinant techniques and peptide synthesis or a combination of these techniques), or may be isolated from an endogenous source of the protein. In certain embodiments of the invention, the protein having an Fc region is an antigen-binding polypeptide, more preferably, an antibody. The antibody can be, for example, a polyclonal antibody preparation, a monoclonal antibody, a recombinant antibody, a chimeric antibody, a humanized antibody or a human antibody. Techniques for the production of an antigen-binding polypeptide, and in particular, antibodies, are described below. Alternatively, the protein having an Fc region can be a modified form of an antibody, such as a bispecific antibody, an antibody conjugate or an antibody fusion protein (e.g., an Fc fusion protein). Techniques for the production of such modified forms of antibodies and antibody fusion proteins also are described below.

Polyclonal Antibodies

Polyclonal antibodies can be prepared by immunizing a suitable subject with an immunogen. The antibody titer in the immunized subject can be monitored over time by standard techniques, such as with an enzyme linked immunosorbent assay (ELISA) using immobilized target antigen. If desired, the antibody molecules directed against the target antigen can be isolated from the mammal (for example, from the blood) and further purified by well known techniques, such as protein A Sepharose chromatography to obtain the antibody, for example, IgG, fraction. At an appropriate time after immunization, for example, when the anti-antigen antibody titers are highest, antibody-producing cells can be obtained from the subject and used to prepare monoclonal antibodies by standard techniques, such as the hybridoma technique originally described by Kohler and Milstein (1975) Nature 256:495-497) (see also, Brown et al. (1981) J. Immunol. 127:539-46; Brown et al. (1980) J. Biol. Chem 255:4980-83; Yeh et al. (1976) Proc. Natl. Acad. Sci. USA 76:2927-31; and Yeh et al. (1982) Int. J. Cancer 29:269-75). For the preparation of chimeric polyclonal antibodies, see Buechler et al. U.S. Pat. No. 6,420,113.

Monoclonal Antibodies

Any of the many well known protocols used for fusing lymphocytes and immortalized cell lines can be applied for the purpose of generating a monoclonal antibody (see, for example, G. Galfre et al. (1977) Nature 266:55052; Gefter et al. Somatic Cell Genet., cited supra; Lerner, Yale J. Biol. Med., cited supra; Kenneth, Monoclonal Antibodies, cited supra). Moreover, the ordinarily skilled worker will appreciate that there are many variations of such methods which also would be useful. Typically, the immortal cell line (for example, a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, for example, the P3-NS1/1-Ag4-1, P3-x63-Ag8.653 or Sp2/O—Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind a target antigen using a standard ELISA assay.

Recombinant Antibodies

Alternative to preparing monoclonal antibody-secreting hybridomas, a monoclonal antibody can be identified and isolated by screening a recombinant combinatorial immunoglobulin library (for example, an antibody phage display library) with a target antigen to thereby isolate immunoglobulin library members that bind the target antigen. Kits for generating and screening phage display libraries are commercially available (for example, the Pharmacia *Recombinant Phage Antibody System*, Catalog No. 27-9400-01; and the Stratagene *SurfZAP*™ *Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J* 12:725-734; Hawkins et al. (1992) *J. Mol. Biol.* 226:889-896; Clarkson et al. (1991) *Nature* 352:624-628; Gram et al. (1992) *Proc. Natl. Acad. Sci. USA* 89:3576-3580; Garrad et al. (1991) *Bio/Technology* 9:1373-1377; Hoogenboom et al. (1991) *Nuc. Acid Res.* 19:4133-4137; Barbas et al. (1991) *Proc. Natl. Acad. Sci. USA* 88:7978-7982; and McCafferty et al. *Nature* (1990) 348:552-554.

Chimeric and Humanized Antibodies

Additionally, recombinant antibodies, such as chimeric and humanized monoclonal antibodies, comprising both human and non-human portions, which can be made using standard recombinant DNA techniques, are within the scope of the invention.

The term "humanized immunoglobulin" or "humanized antibody" refers to an immunoglobulin or antibody that includes at least one humanized immunoglobulin or antibody chain (i.e., at least one humanized light or heavy chain). The term "humanized immunoglobulin chain" or "humanized antibody chain" (i.e., a "humanized immunoglobulin light chain" or "humanized immunoglobulin heavy chain") refers to an immunoglobulin or antibody chain (i.e., a light or heavy chain, respectively) having a variable region that includes a variable framework region substantially from a human immunoglobulin or antibody and complementarity determining regions (CDRs) (for example, at least one CDR, preferably two CDRs, more preferably three CDRs) substantially from a non-human immunoglobulin or antibody, and further includes constant regions (for example, at least one constant region or portion thereof, in the case of a light chain, and three constant regions in the case of a heavy chain). The term "humanized variable region" (for example, "humanized light chain variable region" or "humanized heavy chain variable region") refers to a variable region that includes a variable framework region substantially from a human immunoglobulin or antibody and complementarity determining regions (CDRs) substantially from a non-human immunoglobulin or antibody.

The phrase "substantially from a human immunoglobulin or antibody" or "substantially human" means that, when aligned to a human immunoglobulin or antibody amino acid sequence for comparison purposes, the region shares at least 80-90%, 90-95%, or 95-99% identity (i.e., local sequence identity) with the human framework or constant region sequence, allowing, for example, for conservative substitutions, consensus sequence substitutions, germline substitutions, backmutations, and the like. The introduction of conservative substitutions, consensus sequence substitutions, germline substitutions, backmutations, and the like, is often referred to as "optimization" of a humanized antibody or chain. The phrase "substantially from a non-human immunoglobulin or antibody" or "substantially non-human" means having an immunoglobulin or antibody sequence at least 80-95%, preferably at least 90-95%, more preferably, 96%, 97%, 98%, or 99% identical to that of a non-human organism, for example, a non-human mammal.

Accordingly, all regions or residues of a humanized immunoglobulin or antibody, or of a humanized immunoglobulin or antibody chain, except the CDRs, are substantially identical to the corresponding regions or residues of one or more native human immunoglobulin sequences. The term "corresponding region" or "corresponding residue" refers to a region or residue on a second amino acid or nucleotide sequence which occupies the same (i.e., equivalent) position as a region or residue on a first amino acid or nucleotide sequence, when the first and second sequences are optimally aligned for comparison purposes.

The term "significant identity" means that two polypeptide sequences, when optimally aligned, such as by the programs GAP or BESTFIT using default gap weights, share at least 50-60% sequence identity, preferably at least 60-70% sequence identity, more preferably at least 70-80% sequence identity, more preferably at least 80-90% sequence identity, even more preferably at least 90-95% sequence identity, and even more preferably at least 95% sequence identity or more (for example, 99% sequence identity or more). The term "substantial identity" means that two polypeptide sequences, when optimally aligned, such as by the programs GAP or BESTFIT using default gap weights, share at least 80-90% sequence identity, preferably at least 90-95% sequence identity, and more preferably at least 95% sequence identity or more (for example, 99% sequence identity or more). For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, for example, by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., Current Protocols in Molecular Biology). One example of algorithm that is suitable for determining percent sequence identity and sequence similarity is the BLAST algorithm, which is described in Altschul et al., *J. Mol. Biol.* 215:403 (1990). Software for performing BLAST analyses is publicly available through the National Center for Biotechnology Information (publicly accessible through the National Institutes of Health NCBI internet server). Typically, default program parameters can be used to perform the sequence comparison, although customized parameters can also be used. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

Preferably, residue positions which are not identical differ by conservative amino acid substitutions. For purposes of classifying amino acids substitutions as conservative or non-conservative, amino acids are grouped as follows: Group I (hydrophobic sidechains): leu, met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Preferably, humanized immunoglobulins or antibodies bind antigen with an affinity that is within a factor of three, four, or five of that of the corresponding non-humanized antibody. For example, if the nonhumanized antibody has a binding affinity of $10^{-9}$ M, humanized antibodies will have a binding affinity of at least $3 \times 10^{-8}$ M, $4 \times 10^{-8}$ M, $5 \times 10^{-8}$ M, or $10^{-9}$ M. An immunoglobulin chain is said to "direct antigen binding" when it confers upon an intact immunoglobulin or antibody (or antigen binding fragment thereof) a specific binding property or binding affinity. A mutation (for example, a backmutation) is said to substantially affect the ability of a heavy or light chain to direct antigen binding if it affects (for example, decreases) the binding affinity of an intact immunoglobulin or antibody (or antigen binding fragment thereof) comprising said chain by at least an order of magnitude compared to that of the antibody (or antigen binding fragment thereof) comprising an equivalent chain lacking said mutation. A mutation "does not substantially affect (for example, decrease) the ability of a chain to direct antigen binding" if it affects (for example, decreases) the binding affinity of an intact immunoglobulin or antibody (or antigen binding fragment thereof) comprising said chain by only a factor of two, three, or four of that of the antibody (or antigen binding fragment thereof) comprising an equivalent chain lacking said mutation.

The term "chimeric immunoglobulin" or antibody refers to an immunoglobulin or antibody whose variable regions derive from a first species and whose constant regions derive from a second species. Chimeric immunoglobulins or antibodies can be constructed, for example by genetic engineering, from immunoglobulin gene segments belonging to different species. The terms "humanized immunoglobulin" or "humanized antibody" are not intended to encompass chimeric immunoglobulins or antibodies, as defined infra. Although humanized immunoglobulins or antibodies are chimeric in their construction (i.e., comprise regions from more than one species of protein), they include additional features (i.e., variable regions comprising donor CDR residues and acceptor framework residues) not found in chimeric immunoglobulins or antibodies, as defined herein.

Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Canc. Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *BioTechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

Human Antibodies from Transgenic Animals and Phage Display

Alternatively, it is now possible to produce transgenic animals (for example, mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice results in the production of human antibodies upon antigen challenge. See, for example, U.S. Pat. Nos. 6,150,584; 6,114,598; and 5,770,429.

Fully human antibodies can also be derived from phage-display libraries (Hoogenboom et al., J. Mol. Biol., 227:381 (1991); Marks et al., J. Mol. Biol., 222:581-597 (1991)). Chimeric polyclonal antibodies can also be obtained from phage display libraries (Buechler et al. U.S. Pat. No. 6,420,113).

Bispecific Antibodies and Antibody Conjugates

Bispecific antibodies (BsAbs) are antibodies that have binding specificities for at least two different epitopes. Such antibodies can be derived from full length antibodies or antibody fragments (for example F(ab)'2 bispecific antibodies). Methods for making bispecific antibodies are known in the art. Traditional production of full length bispecific antibodies is based on the coexpression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of different antibody molecules (see, WO 93/08829 and in Traunecker et al., EMBO J., 10:3655-3659 (1991)).

Bispecific antibodies also include cross-linked or "heteroconjugate" antibodies. For example, one of the antibodies in the heteroconjugate can be coupled to avidin, the other to biotin or other payload. Heteroconjugate antibodies may be made using any convenient cross-linking methods. Suitable cross-linking agents are well known in the art, and are disclosed in U.S. Pat. No. 4,676,980, along with a number of cross-linking techniques.

In yet another embodiment, the antibody can be conjugated, chemically or genetically, to a payload such as a reactive, detectable, or functional moiety, for example, an immunotoxin to produce an antibody conjugate. Such payloads include, for example, immunotoxins, chemotherapeutics, and radioisotopes, all of which are well-known in the art.

Antibody Fusion Proteins

A protein having an Fc region as used in the invention can be a fusion protein that contains at least the Fc portion of an antibody fused to a non-antibody protein or polypeptide. For example, the Fc region can be fused to a ligand for a receptor such that a soluble fusion protein is created that is capable of binding the receptor and that has Fc-related functions (such as serum stability, Fc receptor binding and the like). Alternatively, the Fc region can be fused to the extracellular domain of a receptor such that a soluble fusion protein is created that is capable of binding the ligand for the receptor (thereby competing with the native receptor) and that has Fc-related functions. A non-limiting example of such an Fc fusion protein is etanercept (Embrel®), which comprises the extracellular ligand-binding domain of the human TNFα receptor fused to the Fc portion of human IgG1. Antibody fusion proteins (also referred to in the art as Fc fusion proteins or Ig fusion proteins) can be prepared using standard recombinant DNA techniques and have been described in the art, see for example U.S. Pat. No. 5,116,964, U.S. Pat. No. 5,225,538, U.S. Pat. No. 5,336,603 and U.S. Pat. No. 5,428,130, all by Capon et al.

Anti IL-13 Antibodies

In a preferred embodiment, the protein having an Fc region to be purified according to the invention is an anti-IL-13 antibody. Anti-IL-13 antibodies are described in U.S. Provisional Application Ser. Nos. 60/578,473, filed Jun. 9, 2004 and 60/581,375, filed Jun. 22, 2004, both titled "Antibodies against human IL-13 and uses thereof." The contents of these applications are incorporated by reference. A preferred anti-IL-13 antibody may variously be referred to as "IMA" herein.

Antibodies that are capable of binding to, neutralizing and/or inhibiting one or more IL-13-associated activities, particularly the signaling activity of IL-13, are useful for treating IL-13-mediated diseases, such as allergic asthma, nonallergic asthma, and asthma-related pathologies, such as fibrosis, eosinophilia, and mucus production.

IL-13 binding agents that are IL-13 antagonists, including antibodies and antigen-binding fragments thereof that bind to IL-13, in particular, human IL-13, with high affinity and specificity. The antibodies and antigen-binding fragments thereof of the present disclosure are also referred to herein as "anti-IL-13 antibodies" and "fragments thereof," respectively. In one embodiment, the anti-IL-13 antibody or fragment thereof reduces, neutralizes, and/or antagonizes at least one IL-13-associated activity. For example, the anti-IL-13 antibody or fragment thereof can bind to IL-13, e.g., an epitope of IL-13, and interfere with an interaction, e.g., binding, between IL-13 and an IL-13 receptor complex ("IL-13R"), e.g., a complex comprising IL-13 receptor ("IL-13Rα1") and the interleukin-4 receptor alpha chain ("IL-4Rα"), or a subunit thereof (e.g., IL-13Rα1 or IL-4Rα, individually). Thus, the antibodies and fragments thereof described herein can be used to interfere with (e.g., inhibit, block or otherwise reduce) an interaction, e.g., binding, between IL-13 and an IL-13 receptor complex, or a subunit thereof, thereby interfering with the formation of a functional signaling complex.

Other Preferred Fc Region Containing Proteins

In another preferred embodiment, the protein having an Fc region to be purified according to the invention is an anti-Aβ antibody. Anti-Aβ antibodies are described in PCT Publication No. WO 2002/46237 and U.S. Publication No. 20050118651, both titled "Humanized antibodies that recognize beta amyloid peptide." The contents of these applications are incorporated by reference. Preferred anti-Aβ antibodies may variously be referred to as "AAB" and "12A 11" herein.

Other preferred Fc region containing proteins include antibodies that have been approved for therapeutic use in humans. Such antibodies include antibodies that bind to a tumor cell antigen, antibodies that bind to a cytokine, antibodies that bind to a cytokine receptor and antibodies that bind to an adhesion protein. Accordingly, in various embodiments, an Fc region containing protein can be an antibody or an Fc fusion proteins that bind an antigen selected from the group consisting of CD3 (e.g., OKT3), CD52 (e.g., alemtuzumab; Campath®), VEGF (e.g., bevacizumab; Avastin®), EGFR (e.g., cetuximab; Erbitux®), CD33 (e.g., gemtuzumab; Mylotarg®), CD20 (e.g., rituximab; Rituxan®; tositumomab; Bexxar®; ibritumomab; Zevalin®), HER-2 (e.g., trastuzumab; Herceptin®), TNFα (e.g., adalimumab; Humira®, infliximab; Remicade®; etanercept; Embrel®), CD25 (e.g., daclizumab; Zenapax®; basiliximab; Simulect®), RSV (e.g., palivizumab; Synagis®), IgE (e.g., omalizumab; Xolair®), gp IIb/IIIa (e.g., abciximab; Reopro®), CD11a (e.g., efalizumab; Raptiva®) and α4 integrin (e.g., natalizumab; Tysabri®).

It is understood that any of the foregoing polypeptide molecules, alone or in combination, are suitable for preparation as Fc region containing proteins according to the invention.

Various aspects and embodiments of the present invention are further described by way of the following Examples. The Examples are offered by way of illustration and not by way of limitation.

EXAMPLES

The following examples are offered for illustrative purposes only. Examples are provided using three different monoclonal antibodies (referred to as AAB, 12A11 and IMA). Eight separate experiments are described, each representing a combination of antibody and impurity removal.

Materials and Methods

In general, the practice of the present invention employs, unless otherwise indicated, conventional techniques of chemistry, molecular biology, recombinant DNA technology, immunology (especially, e.g., immunoglobulin technology), and standard techniques in electrophoresis. See, e.g., Sambrook, Fritsch and Maniatis, Molecular Cloning: Cold Spring Harbor Laboratory Press (1989); Antibody Engineering Protocols (Methods in Molecular Biology), 510, Paul, S., Humana Pr (1996); Antibody Engineering: A Practical Approach (Practical Approach Series, 169), McCafferty, Ed., Irl Pr (1996); Antibodies: A Laboratory Manual, Harlow et al., C.S.H.L. Press, Pub. (1999); Current Protocols in Molecular Biology, eds. Ausubel et al., John Wiley & Sons (1992). Bousse et al., Protein Sizing on a Microchip, *Anal. Chem.* 73, 1207-1212 (2001); Knapp et al., Commercialized and Emerging Lab-on-a-Chip Applications; In: *Proceedings of the µTAS* 2001 *Symposium*, Ramsey, J. M. & van den Berg, A., 7-10 (2001); and Mhatre et al., Strategies for locating disulfide bonds in a monoclonal antibody via mass spectrometry, *Rapid Commun. Mass Spectrom,* 13 (24) 2503-2510 (1999).

Production of Target Protein

The target Fc containing proteins can be produced by standard expression methods, e.g., using a recombinant mammalian cell line grown in suspension culture. Conditioned medium containing the Fc containing protein of interest is generated in a production bioreactor. The resulting product may be harvested and clarified with any appropriate clarification step such as, for example, either microfiltration and 0.22 µm filtration or centrifugation, pad filtration and 0.22 µm filtration.

Purification of Target Protein

The purification of the target monoclonal antibodies exemplified herein (AAB, 12A11 and IMA) consists of capture of the target molecule on protein A affinity chromatography. This can consist of rmp Protein A Sepharose™ Fast Flow, Protein A Sepharose™ Fast Flow, or MabSelect Protein A.

The resin is then washed as described for each of the experiments and the product eluted and tested for impurity levels.

Analysis of Target Protein

Reversed-Phase HPLC (RP-HPLC) was used to quantitate the amount of IRT present in the AAB monoclonal antibody samples, while Pro A HPLC method was employed to determine IRT levels for the IMA monoclonal antibody. Size Exclusion Chromatography (SEC-HPLC) was used to determine the percentage of monomeric protein (monomeric IgG), high molecular weight (HMW), and low molecular weight (LMW) species. Denaturing SEC-HPLC analysis was carried out to determine the relative amount of Under-Disulfide Bonded (UDB) species in samples. The levels of HCP in the test samples were determined using an Enzyme-Linked immunosorbant assay (ELISA).

Analytical Assays: IRT & UDB

Reversed-Phase HPLC (AAB IRT Analysis)

The RP-HPLC was conducted as follows. Disulfide reduction of each sample was performed by incubation at 40° C. for 60 min in the presence of 2.5 mM DTT. Alkylation was performed by incubation at room temperature in the presence of 5.5 mM iodoacetic acid. Following reduction and alkylation, all samples were quenched with 5 µl of 1 M DTT. The limit of quantification for this assay is 0.5%. Approximately 40 µg of each reduced, alkylated sample was injected onto a POROS R1/H RP-HPLC column and run for 70 min under the following conditions:

Column: Poros R1/H RP-HPLC
Column Temp: 50° C.;
Mobile Phase A: 0.1% TFA (w/v) in water;
Mobile Phase B: 0.1% TFA (w/v) in 95% acetonitrile;
Flow rate: 1.0 mL/min
Detection: 217 nm
Run Time: 70 minutes
Injection: Triplicate of 40 µg each The gradient times were as listed in TABLE 1.

TABLE 1

Gradient times for RP-HPLC method

| Gradient Time | % A | % B |
|---|---|---|
| 0-1 | 95 | 5 |
| 2 | 70 | 30 |
| 54 | 60 | 40 |
| 55.1-70 | 95 | 5 |

Protein A HPLC (IMA IRT Analysis)

The Protein A-HPLC was conducted as follows. A total of 100 µg per injection on POROS Pro A column at room temperature for 35 minutes was performed under the following conditions:

Column: Poros Pro A 4.6×50 mm
Column Temp: ambient
Mobile Phase A: 50 mM Ammonium formate, pH 6.0
Mobile Phase B: 10 mM Ammonium formate, 0.8% formic acid
Flow rate: 2.0 mL/min
Detection: 280 nm
Run Time: 35 minutes
Injection: Triplicate of 100 µg each The gradient times were as listed in table 2.

TABLE 2

Gradient times for Pro A column

| Gradient Time | % A | % B |
|---|---|---|
| 0-5 | 100 | 0 |
| 25-30 | 55 | 45 |
| 30.5-35 | 100 | 0 | dSEC-HPLC (AAB UDB Analysis)

Denaturing SEC-HPLC was conducted as follows. The pretreatment of samples for the denaturing SEC assay involves a reagent/sample mixture at final concentrations of 200 µg/mL of protein, 3 M Guanidine HCl, and 100 mM Tris, at a pH of 7.4. The samples were heated at 80° C. for 20 minutes while mixing through inversion. For this assay, two controls are employed to allow a bracketing of UDB levels. Internal references with low and high levels of UDB were used as controls. Chromatographic/Assay conditions were as follows:

Column: Tosoh BioSep G3000 SWxl
Column Temp: Ambient
Mobile Phase: 3 M Guanidine HCl, 25 mM NaPO$_4$, pH 6.8
Gradient: Isocratic
Flow rate: 0.5 mL/min
Detection: 280 nm
Run Time: 50 minutes
Injection: Triplicate 50 µL (10 µg)

Example 1

Comparison of Wash Buffers for IRT Removal (AAB)

In this example, an impure solution containing the monoclonal antibody AAB was purified by adsorption onto a Protein A column followed by a first wash with a wash buffer containing either CaCl$_2$, MgCl$_2$, NaCl or propylene glycol.

The culture containing the monoclonal antibody was purified at small scale using an rmp Protein A Sepharose™ FF column (8.9 mL) connected to a GE Healthcare ÄKTA FPLC chromatography system. For all the rmp Protein A Sepharose™ FF chromatography steps described in experiment 1, the following conditions were used. (Exceptions are noted in the individual experimental descriptions).

Column dimensions—1.0 cm×11.4 cm

Operational flow rate—150 cm/hr

Equilibration 1-20 mM Tris, 150 mM NaCl, pH 7.5 (5 column volumes)

Flush—20 mM Tris, 150 mM NaCl, pH 7.5 (1 column volume)

Wash 1—Variable (See Table 3) except for run #1, which had no wash 1

Wash 2—20 mM Tris, 1.0 M NaCl, pH 7.5 (5 column volumes)

Wash 3—10 mM Tris, 75 mM NaCl, pH 7.5 (7 column volumes)

Elution—50 mM Glycine, 75 mM NaCl, pH 3.1 (6 column volumes)

Strip 1—20 mM Sodium Citrate, pH 2.7 (5 column volumes)

Strip 2—6 M Guanidine HCl (2 column volumes)

Strip wash—20 mM Tris, 150 mM NaCl, pH 7.5 (5 column volumes)

Storage—16% Ethanol (5 column volumes)

Run temperature: 2-8° C.

The rmp Protein A Sepahrose™ FF column runs were equilibrated with 5 column volumes of 20 mM Tris, 150 mM NaCl, pH 7.5. The column was loaded at approximately 10 mg product/mL resin. Loading was followed by a 1 column volume flush with equilibration buffer and 5 column volumes of wash 1 solution. All Wash 1 solutions tested are outlined in Table 3. Wash 1 was included in all runs except for run #1. Wash 1 was followed by 5 column volumes of 20 mM Tris, 1.0 M NaCl, pH 7.5 and 7 column volumes of 10 mM Tris, 75 mM NaCl, pH 7.5. The monoclonal antibody was eluted from the column with 50 mM Glycine, 75 mM NaCl, pH 3.1. The product pool was then neutralized to 7.9-8.1 with 2 M Tris pH 8.5. The columns were then stripped, washed and stored. Table 3 lists the levels of the IRT species & LMW present in the product pools from the various runs.

TABLE 3

IRT and LMW Values for Various Wash 1 Buffers

| Run # | Condition | % LMW | % IRT |
|---|---|---|---|
| 1 | Control (No Wash 1) | 4.4 | 2.5 |
| 2 | 20% Propylene Glycol, pH 7.5 | 4.7 | 2.5 |
| 3 | 50 mM Tris, 2.0 M Magnesium Chloride, pH 7.5 | 1.6 | 1.5 |
| 4 | 50 mM Tris, 2.5 M Magnesium Chloride, pH 7.5 | 1.5 | 1.3 |
| 5 | 50 mM Acetate, 2.0 M Magnesium Chloride, pH 4.5 | 0.9 | 0.8 |
| 6 | 50 mM Tris, 4.0 M Sodium Chloride, pH 7.5 | 4.4 | 2.5 |
| 7 | 50 mM Tris, 2.0 M Calcium Chloride, pH 7.5 | 1.8 | 1.4 |
| 8 | 50 mM Tris, 2.5 M Calcium Chloride, pH 7.5 | 0.8 | 0.8 |

The results showed that the magnesium chloride and calcium chloride washes reduced levels of IRT and LMW species, whereas the sodium chloride and propylene glycol washes did not reduce IRT or LMW species.

Example 2

Protein A Chromatography with $CaCl_2$ Wash for IRT Removal

In this example, a larger scale antibody purification was carried out using protein A chromatography with a $CaCl_2$ wash to remove IRT species.

The culture containing the monoclonal antibody was purified at pilot scale using a MabSelect Protein A column (2.4 L) connected to a Millipore K-Prime 400 chromatography system. The two MabSelect runs were performed as described below.

Column dimensions—13 cm×18 cm

Operational flow rate—150 cm/hr, 300 cm/hr

Equilibration 1—20 mM Tris, 150 mM NaCl, pH 7.5 (5 column volumes)

Flush—20 mM Tris, 150 mM NaCl, pH 7.5 (2 column volumes)

Wash 1—50 mM Tris, 2 M $CaCl_2$, pH 7.5 for run #1 and no wash 1 for run #2

Wash 2—20 mM Tris, 1.0 M NaCl, pH 7.5 (5 column volumes)

Wash 3—10 mM Tris, 75 mM NaCl, pH 7.5 (5 column volumes)

Elution—50 mM Glycine, 25 mM NaCl, pH 3.1 (6 column volumes)

Strip 1—50 mM Glycine, 0.5 M NaCl, pH 2.7 (5 column volumes)

Strip 2—6 M Guanidine HCl (2 column volumes)

Strip wash—20 mM Tris, 150 mM NaCl, pH 7.5 (5 column volumes)

Storage—16% Ethanol (5 column volumes)

Run temperature: 2-8° C.

The MabSelect Protein A column was equilibrated with 5 column volumes of 20 mM Tris, 150 mM NaCl, pH 7.5. The columns were then loaded at approximately 10 mg product/mL resin. This was followed by a 2 column volume flush with equilibration buffer and 5 column volumes of wash 1 solution. This wash 1 solution consisted of 50 mM Tris, 2.0 M $CaCl_2$, pH 7.5 for run 1, while it was left out entirely for run 2. Wash 1 was then followed by 5 column volumes of 50 mM Tris, 1.0 M NaCl, pH 7.5 and 5 column volumes of 10 mM Tris, 75 mM NaCl, pH 7.5. The monoclonal antibody was eluted from the MabSelect Protein A column with 50 mM Glycine, 25 mM NaCl, pH 3.1. The product pool was then neutralized to 7.8-8.2 with 2 M Tris pH 8.5. The columns were then stripped, washed and stored. The results are shown in Table 4.

TABLE 4

% IRT levels in pilot-scale runs with and without calcium chloride wash

| Run # | Wash 1 Buffer | % IRT |
|---|---|---|
| 1 | 50 mM Tris, 2 M $CaCl_2$, pH 7.5 | 0.8 |
| 2 | Control (None) | 1.9 |

The results showed that at pilot scale the calcium chloride wash removed IRT from the product pool.

Example 3

IRT Removal (IMA)

In this example, a different monoclonal antibody (IMA) from that used in Example 1 was used in a small scale purification with a $CaCl_2$ wash.

The culture containing the different monoclonal antibody (IMA) was purified at small scale using a MabSelect Protein A column (17.3 mL) connected to a GE Healthcare ÄKTA Explorer chromatography system. The run was performed as described below.

Column dimensions—1.1 cm×18.2 cm (17.3 mL)

Operational flow rate—300 cm/hr

Equilibration 1—20 mM Tris, 150 mM NaCl, pH 7.5 (5.1 column volumes)

Wash 1—20 mM Tris, 1 M NaCl, pH 7.5 (5 column volumes)

Wash 2—50 mM Sodium Acetate, 0.6 M $CaCl_2$, pH 5.0 (5 column volumes)

Wash 3—0.50 mM Tris, 5 mM NaCl, pH 7.5 (3 column volumes)

Wash-4—10 mM Tris, 5 mM NaCl, pH 7.5 (5 column volumes)

Elution—50 mM Glycine, 5 mM NaCl, pH 3.0 (5 column volumes)

Strip—6 M Guanidine HCl (5 column volumes)

Strip wash—20 mM Tris, 150 mM NaCl, pH 7.5 (6 column volumes)

Storage—16% Ethanol (5 column volumes)

Run temperature: 18-24° C.

MabSelect protein A column was equilibrated with 5 column volumes of 20 mM Tris, 1 M NaCl, pH 7.5. The column was loaded at approximately 45 mg product/mL resin. The column was then washed as follows: 5 column volumes of 20 mM Tris, 1.0 M NaCl, pH 7.5, 5 column volumes of 50 mM Sodium Acetate, 0.6 M $CaCl_2$, pH 5.0, 3 column volumes of 50 mM Tris, 5 mM NaCl, pH 7.5, and 5 column volumes of 10 mM Tris, 5 mM NaCl, pH 7.5. The product was eluted from the MabSelect protein A column with 50 mM Glycine, 5 mM NaCl, pH 3.0. The product pool was then neutralized to 7.7 with 2 M Tris pH 8.0. The column was then stripped, washed and stored. The results are shown in Table 5, which provides the levels of IRT species in the load and peak.

TABLE 5

| % IRT in the load and peak in run with $CaCl_2$ wash | |
|---|---|
| % IRT in Load | % IRT in Peak |
| 5.8 | 1.1 |

The results showed that the 0.6 M $CaCl_2$ wash provided a 5-fold reduction of IRT.

Example 4

Host Cell Protein Removal (IMA)

In this example, the ability of a $CaCl_2$ wash to remove host cell protein (HCP) from a preparation containing the IMA monoclonal antibody was examined.

The culture containing the monoclonal antibody was purified at small scale using a MabSelect Protein A column (19 mL) connected to a GE Healthcare ÄKTA FPLC chromatography system. The two MabSelect runs were performed as described below.

Column dimensions—1.1 cm×20.0 cm (19 mL)

Operational flow rate—300 cm/hr

Equilibration 1—20 mM Tris, 150 mM NaCl, pH 7.5 (5.0 column volumes)

Wash 1—20 mM Tris, 1 M NaCl, pH 7.5 (5 column volumes)

Wash 2—50 mM Sodium Acetate, 0.6 M $CaCl_2$, pH 5.0 (5 column volumes; only for run 2)

Wash 3—50 mM Tris, 5 mM NaCl, pH 7.5 (2 column volumes)

Wash 4—10 mM Tris, 5 mM NaCl, pH 7.5 (5 column volumes)

Elution—50 mM Glycine, 5 mM NaCl, pH 3.0 (5 column volumes)

Strip—6 M Guanidine HCl (5 column volumes)

Strip wash—20 mM Tris, 150 mM NaCl, pH 7.5 (6 column volumes)

Storage—16% Ethanol (5 column volumes)

Run temperature: 18-24° C.

The MabSelect protein A column was equilibrated with 5 column volumes of 20 mM Tris, 150 mM NaCl, pH 7.5. The column was loaded at approximately 45 mg product/mL resin. The column was then washed with 5 column volumes of 20 mM Tris, 1.0 M NaCl, pH 7.5; for Run 2 an additional wash with 5 column volumes of 50 mM Sodium Acetate, 0.6 M $CaCl_2$, pH 5.0 was used. Prior to elution, the column was then washed with 5 column volumes of 50 mM Tris, 5 mM NaCl, pH 7.5 and 5 column volumes of 10 mM Tris, 5 mM NaCl, pH 7.5. The product was eluted from the MabSelect protein A column with 50 mM Glycine, 5 mM NaCl, pH 3.0. The product pool was then neutralized to pH 7.7 with 2 M Tris pH 8.0. The column was then stripped, washed and stored. The results are shown in Table 6, which provides the level of HCP species present in the control run and the run washed with $CaCl_2$.

TABLE 6

| HCP removal with and without $CaCl_2$ wash | | |
|---|---|---|
| Run # | Wash 2 Condition | HCP (PPM) |
| 1 | None (Control) | 6,124 |
| 2 | 50 mM Sodium Acetate, 0.6 M $CaCl_2$, pH 5.0 | 2,295 |

The results showed that the $CaCl_2$ wash provided 3 fold greater removal of HCP as compared to the control run.

Example 5

DNA Removal (AAB)

In this example, the ability of a $CaCl_2$ wash to remove host cell DNA from a preparation containing the AAB monoclonal antibody was examined.

The culture containing the monoclonal antibody was purified at small scale using a MabSelect Protein A column (19 mL) connected to a GE Healthcare ÄKTA FPLC chromatography system. The three MabSelect runs were performed as described below.

Column dimensions—1.1 cm×20 cm

Operational flow rate—300 cm/hr

Equilibration 1—20 mM Tris, 150 mM NaCl, pH 7.5 (5 column volumes)

Flush—20 mM Tris, 150 mM NaCl, pH 7.5 (2 column volumes)

Wash 1—50 mM Tris, 2.0 M $CaCl_2$, pH 7.5 (5 column volumes) (Runs 2 and 3 only)

Wash 2—20 mM Tris, 1.0 M NaCl, pH 7.5 (5 column volumes) (Runs 1 and 3 only)

Wash 3—10 mM Tris, 75 mM NaCl, pH 7.5 (7 column volumes)

Elution—50 mM Glycine, 75 mM NaCl, pH 3.0 (6 column volumes)

Strip—50 mM Glycine, 0.5 M NaCl, pH 2.7 (5 column volumes)

Strip wash—20 mM Tris, 150 mM NaCl, pH 7.5 (5 column volumes)

Storage—16% Ethanol (5 column volumes)

Run temperature: 18-24° C.

The MabSelect Protein A column runs were equilibrated with 5 column volumes of 20 mM Tris, 150 mM NaCl, pH 7.5. The columns were then loaded at a load of approximately 40 mg product/mL resin. This was followed by a 2 column volume flush with equilibration buffer. For runs 2 and 3, this step was followed by 5 column volumes of Wash 1 solution. For runs 1 and 3, 5 column volumes of Wash 2 solution was used. All 3 runs employed 7 column volumes of Wash 3 solution. The monoclonal antibody was eluted off the MabSelect Protein A column with 50 mM Glycine, 75 mM NaCl, pH 3.0. The product pool was then neutralized to 7.5-8.0 with 2 M Tris pH 8.5. The columns were then stripped, washed and stored. The results are shown in Table 7.

TABLE 7

DNA removal with calcium chloride wash.

| Run # | Wash 1 | Wash 2 | DNA (ng/mL) | DNA (ppm) |
|---|---|---|---|---|
| 1 | None (Control) | 20 mM Tris, 1 M NaCl, pH 7.5 | 3.6 | 0.37 |
| 2 | 50 mM Tris, 2 M CaCl$_2$, pH 7.5 | None | 0.9 | 0.09 |
| 3 | 50 mM Tris, 2 M CaCl$_2$, pH 7.5 | 20 mM Tris, 1 M NaCl, pH 7.5 | 0.3 | 0.03 |

The results showed that the addition of 50 mM Tris, 2.0 M calcium chloride, pH 7.5 provided 10 fold greater reduction of DNA compared to using NaCl in the wash solution.

Example 6

Host Cell Protein (HCP) Removal (12A11)

In this example, a third monoclonal antibody, 12A11, was used in purification runs in which various wash conditions were tested for the ability to remove HCP.

A high throughput screen (HTS) in a 96-well filter plate format was performed to identify the best wash conditions for removal of impurities such as HCP for the MabSelect step. This screen varied the wash excipients, excipient concentration, and pH to determine their effect on process related impurities such as HCP.

The MabSelect resin was equilibrated using 5 mM Tris, 10 mM NaCl, pH 7.3 and loaded with product in a column. The resin was then unpacked, mixed and 50 μL of resin was distributed to each well of a 96 well filter plate. The resin in each well was equilibrated in solution of 5 mM Tris, 10 mM-NaCl, pH 7.3, and then washed with each of the various excipient wash solutions in 3 stages, each using 300 μL of wash buffer. After the excipient wash, a second wash with 5 mM Tris, 10 mM NaCl, pH 7.3 buffer was performed in 4 stages of 300 μL each. The product was then eluted from the resin in 3 stages of 300 μL each. Elution stages 1 and 2 were combined and tested for HCP levels.

Resin Volume—50 μL

Wash Excipients—Sodium Chloride, Calcium Chloride, Magnesium Chloride,

Excipient Concentrations—100, 250, 500, 1000, 1500, and 2000 mM

Excipient pH—6.0 & 7.5

Elution Buffers—25 mM Hepes, 10 mM NaCl, pH 3.0, 25 mM Hepes, 100 mM NaCl, pH 3.0, 50 mM Glycine, 10 mM NaCl, pH 3.0, 50 mM Glycine, 100 mM NaCl, pH 3.0 and 100 mM Arginine, 10 mM NaCl, pH 3.0, 100 mM Arginine, 100 mM NaCl, pH 3.0

Run temperature: 18-24° C.

The results are shown in Tables 8 and 9.

TABLE 8

HCP values for MabSelect resin washed with sodium chloride, calcium chloride, or magnesium chloride at pH 6.0

| Elution Buffer | Elution NaCl Conc. (mM) | Wash Excipient Conc. (mM) | Wash Excipient NaCl HCP (ppm) | CaCl$_2$ HCP (ppm) | MgCl$_2$ HCP (ppm) |
|---|---|---|---|---|---|
| 50 mM Glycine | 10 | 100 | 46,800 | 28,500 | 30,800 |
| 25 mM HEPES | | 250 | 35,300 | 17,900 | 22,000 |
| 100 mM Arginine | | 500 | 40,900 | 17,700 | 18,400 |
| 50 mM Glycine | | 1000 | 34,300 | 12,600 | 14,200 |
| 25 mM HEPES | | 1500 | 37,000 | 7,800 | 10,700 |
| 100 mM Arginine | | 2000 | 43,900 | 5,800 | 9,300 |

TABLE 9

HCP values for MabSelect resin washed with sodium chloride, calcium chloride, or magnesium chloride at pH 7.5.

| Elution Buffer | Elution NaCl Conc. (mM) | Wash Excipient Conc. (mM) | Wash Excipient NaCl HCP (ppm) | CaCl$_2$ HCP (ppm) | MgCl$_2$ HCP (ppm) |
|---|---|---|---|---|---|
| 50 mM Glycine | 100 | 100 | 27,900 | 17,900 | 21,800 |
| 25 mM HEPES | | 250 | 24,700 | 16,600 | 18,200 |
| 100 mM Arginine | | 500 | 26,500 | 14,000 | 17,300 |
| 50 mM Glycine | | 1000 | 30,100 | 14,500 | 17,700 |
| 25 mM HEPES | | 1500 | 35,300 | 12,000 | 12,500 |
| 100 mM Arginine | | 2000 | 41,700 | 8,200 | 11,700 |

The results showed that both calcium chloride and magnesium chloride reduced the level of HCP in the MabSelect peak pool compared to sodium chloride at pH 6.0 (Table 8) and pH 7.5 (Table 9) at all excipient concentrations.

Example 7

Removal of Under-Disulfide Bonded Species (UDB)

In this example, the ability of the CaCl$_2$ wash to remove under disulfide bonded species (UDB) was examined.

Two rmp Protein A Sepharose™ FF runs were performed essentially as described in example 1.

Column dimensions—1.0 cm×11.4 cm

Operational flow rate—150 cm/hr

Equilibration 1—20 mM Tris, 150 mM NaCl, pH 7.5 (5 column volumes)

Flush—20 mM Tris, 150 mM NaCl, pH 7.5 (1 column volume)

Wash 1—50 mM Acetate, 2.0 M CaCl$_2$, pH 5.0 for Run 1; None for Run 2

Wash 2—20 mM Tris, 1.0 M NaCl, pH 7.5 (5 column volumes)

Wash 3—10 mM Tris, 75 mM NaCl, pH 7.5 (7 column volumes)

Elution—50 mM Glycine, 75 mM NaCl, pH 3.1 (6 column volumes)

Strip 1—20 mM Sodium Citrate, pH 2.7 (5 column volumes)

Strip 2—6 M Guanidine HCl (2 column volumes)

Strip wash—20 mM Tris, 150 mM NaCl, pH 7.5 (5 column volumes)

Storage—16% Ethanol (5 column volumes)

Run temperature: 2-8° C.

The rmp Protein A Sepharose FF columns were equilibrated with 5 column volumes of 20 mM Tris, 150 mM NaCl, pH 7.5. The columns were then loaded at a load of approximately 10 mg product/mL resin. This was followed by a 1 column volume flush with equilibration buffer and then 5 column volumes of wash 1 solution. This wash 1 solution consisted of 50 mM Acetate, 2.0 M CaCl$_2$, pH 5.0 for run 1, while it was left out entirely for run 2. Wash 1 was then followed by 5 column volumes of 20 mM Tris, 1.0 M NaCl, pH 7.5 and 7 column volumes of 10 mM Tris, 75 mM NaCl, pH 7.5. The monoclonal antibody was eluted off the rmp Protein A Sepharose™ FF column with 50 mM Glycine, 75 mM NaCl, pH 3.1. The product pool was then neutralized to 7.8-8.2 with 2 M Tris pH 8.5. The columns were then stripped, washed and stored. The results are shown in Table 10.

TABLE 10

% UDB for with and without calcium washed samples.

| Run # | Sample | % UDB |
|---|---|---|
| 1 | 50 mM Acetate, 2.0 M CaCl$_2$, pH 5.0 | 9.5 |
| 2 | None (Control) | 20.8 |

A 2-fold reduction in UDB levels was observed for the run that had the additional 50 mM Acetate, 2.0 M CaCl$_2$, pH 5.0 wash.

Example 8

Removal of HCP and IRT with Other Divalent Cation Salt Washes (AAB)

In this example, the ability of washes containing either MnCl$_2$ or NiCl$_2$ to remove impurities from a preparation containing the AAB monoclonal antibody was examined.

Two runs were performed to evaluate the effect of washes containing other divalent cationic salts such as MnCl$_2$ and NiCl$_2$. Two control runs were also performed—one using a 50 mM Tris, 1.0 M NaCl, pH 7.5 wash (no IRT or HCP removal expected) and another using a 50 mM Tris, 2.0 M CaCl$_2$, pH 7.5 wash.

The culture containing the monoclonal antibody was purified at small scale using a MabSelect Protein A column (9 mL) connected to a GE Healthcare ÄKTA FPLC chromatography system. The MabSelect runs were performed as described below. As described below, all operational parameters were identical for the four runs except for Wash 1, which was variable (Table 11).

Column dimensions—1.0 cm×11.5 cm (9 mL)

Operational flow rate—300 cm/hr (Equilibration, Wash 2, Elution, Regeneration, Storage)

Operational flow rate—230 cm/hr (Load, Flush, Wash 1)

Equilibration 1—50 mM Tris, 150 mM NaCl, pH 7.5 (5.0 column volumes)

Wash 1—Variable (See Table 11 for composition)

Wash 2—50 mM Tris, 10 mM NaCl, pH 7.5 (5 column volumes)

Elution—50 mM Glycine, 10 mM NaCl, pH 3.0 (3 column volumes)

Regeneration—50 mM NaOH, 0.5 M Na$_2$SO$_4$ (5 column volumes)

Storage—16% Ethanol, 50 mM Tris, 150 mM NaCl, pH 7.5 (5 column volumes)

Run temperature: 18-24° C.

The MabSelect Protein A column was equilibrated with 5 column volumes of 50 mM Tris, 150 mM NaCl, pH 7.5. The column was loaded at approximately 40 mg product/mL resin. The remaining load was flushed out of the column with 5 column volumes of 50 mM Tris, 150 mM NaCl, pH 7.5. The column was then washed with one of the solutions described in Table 11. Prior to elution the column was washed with 5 column volumes of 50 mM Tris, 10 mM NaCl, pH 7.5. The product was eluted from the MabSelect Protein A column with 50 mM Glycine, 10 mM NaCl, pH 3.0. The product pool was then neutralized to pH 8.0 with 2 M Tris pH 9.0. The column was stripped with 5 column volumes 50 mM NaOH, 0.5 M Na$_2$SO$_4$ then stored with 5 column volumes of 16% ethanol, 50 mM Tris, 150 mM NaCl, pH 7.5. The results are shown in Table 11 (HCP removal) and Table 12 (IRT removal).

TABLE 11

HCP removal with various wash solutions

| Run # | Wash 1 Condition | HCP (PPM) |
|---|---|---|
| 1 | 50 mM Tris, 1.0 M NaCl, pH 7.5 | 17,600 |
| 2 | 50 mM Sodium Acetate, 1.5 M MnCl$_2$, pH 5.0* | 10,600 |
| 3 | 50 mM Sodium Acetate, 1.5 M NiCl$_2$, pH 5.0* | 4,700 |
| 4 | 50 mM Tris, 2.0 M CaCl$_2$, pH 7.5 | 6,500 |

*pH 5.0 was chosen due to solubility of MnCl$_2$ and NiCl$_2$

TABLE 12

IRT Removal with various wash solutions

| Run # | Wash 1 Condition | IRT (%) |
|---|---|---|
| 1 | 50 mM Tris, 1.0 M NaCl, pH 7.5 | 2.78 |
| 2 | 50 mM Sodium Acetate, 1.5 M MnCl$_2$, pH 5.0* | 0.77 |
| 3 | 50 mM Sodium Acetate, 1.5 M NiCl$_2$, pH 5.0* | 0.47 |
| 4 | 50 mM Tris, 2.0 M CaCl$_2$, pH 7.5 | 0.87 | pH 5.0 was chosen due to solubility of MnCl$_2$ and NiCl$_2$

Table 11 shows that the level of HCPs present in runs that were washed with solutions containing divalent cations had 1.5-3.5 fold less HCPs than the control (1.0 M NaCl Wash). Table 12 shows that the runs that contained the washes with divalent cationic salts solutions also provide>3.5 fold IRT removal compared to the run with a 1.0 M NaCl containing wash solutions. Thus, these results demonstrated that salt washes with other divalent cations (e.g., with MnCl$_2$ or NiCl$_2$), different than CaCl$_2$, also were effective in removing impurities.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method for purifying a protein having an Fc region from a source liquid comprising the protein and one or more impurities, comprising the steps of:
    adsorbing the protein to an Fc binding agent;
    washing the Fc binding agent bound to the protein with a buffer solution containing CaCl$_2$ at a concentration from about 0.5 M to about 3 M to reduce the one or more impurities; and
    recovering the protein from the Fc binding agent in an elution solution, wherein the protein having an Fc region is purified from the source liquid.

2. The method of claim 1, wherein said one or more impurities are selected from the group consisting of: intron read through variant species (IRT), under disulfide bonded species (UDB), and low molecular weight species (LMW).

3. The method of claim 2, wherein said one or more impurities is an IRT.

4. The method of claim 1, wherein the protein is an antibody that binds to an antigen selected from the group consisting of: CD3, CD52, VEGF, EGFR, CD33, CD20, HER-2, TNFα, CD25, RSV, IgE, gp IIb/IIIa, CD11a and α4 integrin.

5. The method of claim 1, wherein the protein is an anti-IL-13 antibody.

6. The method of claim 1, wherein the protein having an Fc region is recombinantly produced.

7. The method of claim 1, wherein the protein having an Fc region is recombinantly produced in a Chinese Hamster Ovary (CHO) cell.

8. The method of claim 1, wherein the Fc binding agent comprises one or more of Protein A and Protein G.

9. The method of claim 1, wherein the Fc binding agent is immobilized on a solid phase.

10. The method of claim 9, wherein the solid phase comprises one or more of a bead, a gel, a resin, and a particle.

11. The method of claim 1, wherein the buffer solution containing the CaCl$_2$ has a pH value in a range between about 4 to about 8.

12. The method of claim 1, wherein the buffer solution containing the CaCl$_2$ has a pH value in a range between about 4.5 to about 7.5.

13. The method of claim 1, wherein the buffer solution has a CaCl$_2$ concentration in a range between about 1 M to about 3 M.

14. The method of claim 13, wherein the buffer solution has a CaCl$_2$ concentration in a range between about 0.6 M to about 2.5 M.

15. The method of claim 1, wherein the buffer solution has a CaCl$_2$ concentration in a range between about 1.5 M to about 2.5 M.

16. The method of claim 1, wherein the buffer solution containing CaCl$_2$ comprises about 2 M CaCl$_2$.

17. The method of claim 1, wherein the steps of adsorbing the protein to an Fc binding agent and washing the Fc binding agent are performed at a temperature in the range between about 2° C. to about 24° C.

18. The method of claim 1, wherein the one or more impurities comprise one or more of a host cell protein, a host cell DNA, a cell culture protein, and mixtures thereof.

19. The method of claim 1, wherein the one or more impurities comprise an undesired species of the protein having an Fc region.

20. The method of claim 19, wherein the undesired species of the protein having an Fc region comprises one or more of antibody chains or fragments thereof having an intronic read through sequence, one or more antibody chains or fragments thereof having an improper disulfide linkage, a half-antibody or fragment thereof, a light chain dimer or fragment thereof, and a heavy chain dimer or fragment hereof.

21. The method of claim 1, wherein the step of recovering the protein from the Fc binding agent comprises eluting the protein using an elution buffer having a pH in a range from about 2.0 to about 6.5.

22. The method of claim 1, wherein the method further comprises a chromatography step selected from the group consisting of: anion exchange chromatography, cation exchange chromatography, immobilized metal affinity chromatography and hydrophobic interaction chromatography (HIC).

23. The method of claim 1, wherein the method further comprises a step selected from the group consisting of: hydroxyapatite chromatography, dialysis, affinity chromatography, ammonium sulphate precipitation, ethanol precipitation, reverse phase HPLC (RP-HPLC), and chromatofocusing.

24. The method of claim 1, wherein the one or more impurities comprise one or more intron read-through variants of the protein and the elution solution containing the protein has a level of intron read-through variants that is at least 5 fold less than the level of intron read-through variants in the source liquid.

25. The method of claim 24, wherein a solution containing the protein recovered in the elution solution has a level of intron read-through variants that is at least 10 fold less than the level of intron read-through variants in the source liquid.

26. The method of claim 1, wherein the one or more impurities comprise one or more intron read-through variants of the protein and the intron read-through variants comprise less than about 1% of a species of said protein in the elution solution.

27. The method of claim 26, wherein the intron read-through variants comprise less than about 0.8% of a species of said protein in the elution solution.

28. The method of claim 27, wherein the intron read-through variants comprise less than about 0.5% of the species of said protein in the elution solution.

29. The method of claim 28, wherein the intron read-through variants comprise less than about 0.2% of a species of said protein in the elution solution.

30. The method of claim 1, wherein the one or more impurities comprise one or more low molecular weight species of the protein and the low molecular weight species comprise less than about 1% of a species of said protein in the elution solution.

31. The method of claim 30, wherein the low molecular weight species comprise less than about 0.8% of a species of said protein in the elution solution.

32. The method of claim 31, wherein the low molecular weight species comprise less than about 0.5% of a species of said protein in the elution solution.

33. The method of claim 32, wherein the low molecular weight species comprise less than about 0.2% of a species of said protein in the elution solution.

34. The method of claim 1, wherein the one or more impurities comprise one or more under-disulfide bonded variants of the protein and the under-disulfide bonded variants comprise less than about 15% of a species of said protein in the elution solution.

35. The method of claim 34, wherein the under-disulfide bonded variants comprise less than about 10% of a species of said protein in the elution solution.

36. The method of claim 35, wherein the under-disulfide bonded variants comprise less than about 5% of a species of said protein in the elution solution.

37. The method of claim 36, wherein the under-disulfide bonded variants comprise less than about 2% of a species of said protein in the elution solution.

38. The method of claim 1, wherein the Fc binding agent is a protein selected from the group consisting of: Protein A, Protein G, and Protein A/G.

39. The method of claim 1, wherein the Fc binding agent is a moiety that binds selectively or preferentially to the protein through a specific interaction with a binding site of the protein.

40. The method of claim 1, further comprising washing the Fc binding agent bound to the protein having an Fc region with a buffer solution containing NaCl at a concentration of from 0.75 M to 2.0 M after washing with the $CaCl_2$, wherein said one or more impurities is selected from the group consisting of: intron read through variant species (IRT), under disulfide bonded species (UDB), low molecular weight species (LMW), host cell protein and host cell DNA.

41. The method of claim 1, wherein said one or more impurities is selected from the group consisting of: intron read through variant species (IRT), under disulfide-bonded species (UDB), and low molecular weight species (LMW), and wherein the one or more impurities is reduced to a level of at least about 2-fold lower than that present in the source liquid.

42. A method for purifying a protein having an Fc region from a source liquid comprising the protein and one or more impurities, wherein the one or more impurities comprise one or more intron read through variant species (IRT), the method comprising the steps of:
adsorbing the protein having an Fc region to an affinity ligand which is an Fc binding agent;
washing the affinity ligand with a buffer solution containing $CaCl_2$ at a concentration from about 0.5 M to about 3 M to reduce the IRT; and
recovering the protein having an Fc region from the affinity ligand in an elution solution, wherein the protein having an Fc region is purified from the source liquid.

43. The method of claim 42, wherein the buffer solution containing the $CaCl_2$ has a pH value in a range between about 4 to about 8.

44. The method of claim 42, wherein the buffer solution containing the $CaCl_2$ has a pH value in a range between about 4.5 to about 7.5.

45. The method of claim 42, wherein the buffer solution has a $CaCl_2$ concentration in a range between about 1 M to about 3 M.

46. The method of claim 45, wherein the buffer solution has a $CaCl_2$ concentration in a range between about 1.5 M to about 2.5 M.

47. The method of claim 42, wherein the buffer solution containing $CaCl_2$ comprises about 2 M $CaCl_2$.

48. The method of claim 42, wherein the protein having an Fc region is recombinantly produced.

49. The method of claim 48, wherein the protein having an Fc region is recombinantly produced in a Chinese Hamster Ovary (CHO) cell.

50. The method of claim 42, wherein the Fc binding agent is a protein selected from the group consisting of: Protein A, Protein G and Protein A/G.

51. The method claim 42, wherein the Fc binding agent is immobilized on a solid phase.

52. The method of claim 42, wherein the steps of adsorbing the protein having an Fc region to an Fc binding agent and washing the Fc binding agent are performed at a temperature in the range between about 2° C. to about 24° C.

53. The method of claim 42, wherein the step of recovering the protein having an Fc region from the Fc binding agent comprises eluting the protein using an elution buffer having a pH in a range from about 2.0 to about 6.5.

54. The method of claim 42, wherein the method further comprises a chromatography step selected from the group consisting of: anion exchange chromatography, cation exchange chromatography, immobilized metal affinity chromatography and hydrophobic interaction chromatography (HIC).

55. The method of claim 42, wherein the method further comprises a step selected from the group consisting of: hydroxyapatite chromatography, dialysis, affinity chromatography, ammonium sulphate precipitation, ethanol precipitation, reverse phase HPLC (RP-HPLC), and chromatofocusing.

56. The method of claim 42, wherein the elution solution containing the protein having an Fc region has a level of intron read-through variants that is at least 5 fold less than the level of intron read-through variants in the source liquid.

57. The method of claim 42, wherein the intron read-through variants comprise less than about 1% of a species of said protein in the elution solution.

58. The method of claim 42, wherein the impurities further comprise at least one of under disulfide bonded species (UDB) and low molecular weight species (LMW).

59. The method of claim 42, wherein the one or more intron read-through variant species (IRT) is reduced to a level of at least about 2-fold lower than that present in the source liquid.

60. The method of claim 42, further comprising washing the Fc binding agent bound to the protein having an Fc region with a buffer solution containing NaCl at a concentration selected from 5 mM or 10 mM after washing with the $CaCl_2$, wherein the one or more impurities comprise one or more intron read through variant species (IRT) or host cell protein.

61. A method for purifying a protein having an Fc region from a source liquid comprising the protein and one or more impurities, wherein the protein having an Fc region is an antibody, the method comprising the steps of:
adsorbing the protein having an Fc region to an affinity ligand which is an Fc binding agent;
washing the affinity ligand with a buffer solution containing $CaCl_2$ at a concentration from about 0.5 M to about 3 M to reduce the one or more impurities; and
recovering the protein having an Fc region from the affinity ligand in an elution solution, wherein the protein having an Fc region is purified from the source liquid.

62. The method of claim 61, wherein said one or more impurities are selected from the group consisting of: intron read through variant species (IRT), under disulfide bonded species (UDB) and low molecular weight species (LMW).

63. The method of claim 61, wherein the antibody is selected from the group consisting of: an antibody fusion, a murine antibody, a chimeric antibody, a humanized antibody and a human antibody.

64. The method of claim 61, wherein the antibody is a humanized antibody.

65. The method of claim 61, wherein the antibody is a humanized IL-13 antibody.

66. The method of claim 61, wherein the protein having an Fc region is recombinantly produced.

67. The method of claim 66, wherein the protein having an Fc region is recombinantly produced in a Chinese Hamster Ovary (CHO) cell.

68. The method of claim 61, wherein the Fc binding agent is a protein selected from the group consisting of: Protein A, Protein G and Protein A/G.

69. The method of claim 61, wherein the Fc binding agent is immobilized on a solid phase.

70. The method of claim 61, wherein the buffer solution containing the $CaCl_2$ has a pH value in a range between about 4 to about 8.

71. The method of claim 61, wherein the buffer solution containing the $CaCl_2$ has a pH value in a range between about 4.5 to about 7.5.

72. The method of claim 61, wherein the buffer solution has a $CaCl_2$ concentration in a range between about 1 M to about 3 M.

73. The method of claim 61, wherein the buffer solution has a $CaCl_2$ concentration in a range between about 1.5 M to about 2.5 M.

74. The method of claim 61, wherein the buffer solution containing $CaCl_2$ comprises about 2 M $CaCl_2$.

75. The method of claim 61, wherein the steps of adsorbing the protein having an Fc region to an Fc binding agent and washing the Fc binding agent are performed at a temperature in the range between about 2° C. to about 24° C.

76. The method of claim 61, wherein the one or more impurities comprise one or more of a host cell protein, a host cell DNA, a cell culture protein, and mixtures thereof.

77. The method of claim 61, wherein the one or more impurities comprise an undesired species of the protein having an Fc region.

78. The method of claim 61, wherein the step of recovering the protein having an Fc region from the Fc binding agent comprises eluting the protein using an elution buffer having a pH in a range from about 2.0 to about 6.5.

79. The method of claim 61, wherein the method further comprises a chromatography step selected from the group consisting of: anion exchange chromatography, cation exchange chromatography, immobilized metal affinity chromatography and hydrophobic interaction chromatography (HIC).

80. The method of claim 61, wherein the method further comprises a step selected from the group consisting of: hydroxyapatite chromatography, dialysis, affinity chromatography, ammonium sulphate precipitation, ethanol precipitation, reverse phase HPLC (RP-HPLC), and chromatofocusing.

81. The method of claim 61, wherein the one or more impurities comprise one or more intron read-through variants of the protein and the elution solution containing the protein has a level of intron read-through variants that is at least 5 fold less than the level of intron read-through variants in the source liquid.

82. The method of claim 61, wherein the one or more impurities comprise one or more intron read-through variants of the protein and the intron read-through variants comprise less than about 1% of a species of said protein in the elution solution.

83. The method of claim 61, wherein the one or more impurities comprise one or more low molecular weight species of the protein and the low molecular weight species comprise less than about 1% of a species of said protein in the elution solution.

84. The method of claim 61, wherein the one or more impurities comprise one or more under-disulfide bonded variants of the protein and the under-disulfide bonded variants comprise less than about 15% of a species of said protein in the elution solution.

85. The method of claim 61, further comprising washing the Fc binding agent bound to the protein having an Fc region with a buffer solution containing NaCl at a concentration of from 0.75 M to 2.0 M after washing with the $CaCl_2$, wherein said one or more impurities is selected from the group consisting of: intron read through variant species (IRT), under disulfide bonded species (UDB), low molecular weight species (LMW), host cell protein and host cell DNA.

86. The method of claim 61, wherein said one or more impurities is selected from the group consisting of: intron read through variant species (IRT), under disulfide-bonded species (UDB), and low molecular weight species (LMW), and wherein the one or more impurities is reduced to a level of at least about 2-fold lower than that present in the source liquid.

* * * * *